US009956168B2

(12) United States Patent
Davis et al.

(10) Patent No.: US 9,956,168 B2
(45) Date of Patent: May 1, 2018

(54) EXTENDED RELEASE DRUG-DELIVERY CONTACT LENSES AND METHODS OF MAKING

(71) Applicant: Mercy Medical Research Institute, Springfield, MO (US)

(72) Inventors: Keela Davis, Springfield, MO (US); Martin Reuter, Flemington, MO (US); Anthony Kammerich, Battlefield, MO (US); Andrew Tangonan, Springfield, MO (US); Kumar Vedantham, Springfield, MO (US); Anna Kelley, Walnut Grove, MO (US)

(73) Assignee: Mercy Medical Research Institute, Springfield, MO (US)

( * ) Notice: Subject to any disclaimer, the term of this patent is extended or adjusted under 35 U.S.C. 154(b) by 0 days. days.

(21) Appl. No.: 14/309,437

(22) Filed: Jun. 19, 2014

(65) Prior Publication Data
US 2014/0377327 A1 Dec. 25, 2014

Related U.S. Application Data

(60) Provisional application No. 61/837,537, filed on Jun. 20, 2013, provisional application No. 61/837,530, filed on Jun. 20, 2013.

(51) Int. Cl.
*A61K 9/00* (2006.01)
*A61K 31/573* (2006.01)
*A61K 31/7052* (2006.01)
*A61K 45/06* (2006.01)
*B29D 11/00* (2006.01)
*G02B 1/04* (2006.01)
*G02C 7/04* (2006.01)

(52) U.S. Cl.
CPC .......... *A61K 9/0051* (2013.01); *A61K 31/573* (2013.01); *A61K 31/7052* (2013.01); *A61K 45/06* (2013.01); *B29D 11/00048* (2013.01); *B29D 11/00096* (2013.01); *G02B 1/043* (2013.01); *A61K 9/0092* (2013.01); *G02C 7/04* (2013.01)

(58) Field of Classification Search
CPC .......... A61L 27/26; A61L 27/34; A61L 27/18; A61L 15/44; A61L 15/60; A61L 31/06; A61L 15/32; A61L 27/24; A61L 31/041; A61L 2300/602; A61L 27/3839; A61L 27/50; A61L 27/507; A61L 27/54; A61L 31/10
See application file for complete search history.

(56) References Cited

U.S. PATENT DOCUMENTS

| | | | |
|---|---|---|---|
| 4,582,884 A | 4/1986 | Ratkowski | |
| 4,919,850 A * | 4/1990 | Blum | B29D 11/00413 264/1.38 |
| 5,106,533 A | 4/1992 | Hendrickson et al. | |
| 5,776,999 A | 7/1998 | Nicolson et al. | |
| 5,840,338 A * | 11/1998 | Roos | A61K 8/042 424/484 |
| 7,329,001 B2 | 2/2008 | Benrashid et al. | |
| 7,795,359 B2 | 9/2010 | Devlin et al. | |
| 8,083,347 B2 * | 12/2011 | Bango, Jr. | A61K 9/0051 351/159.74 |
| 2003/0017208 A1 | 1/2003 | Ignatious et al. | |
| 2003/0193118 A1 | 10/2003 | Bango et al. | |
| 2003/0215624 A1 | 11/2003 | Layman et al. | |
| 2003/0232287 A1 | 12/2003 | Bango | |
| 2004/0018226 A1 * | 1/2004 | Wnek | A61F 2/08 424/443 |
| 2005/0067287 A1 | 3/2005 | Fuerst et al. | |
| 2006/0085063 A1 | 4/2006 | Shastri et al. | |
| 2006/0155253 A1 * | 7/2006 | Dziezok | A61F 13/15203 604/378 |
| 2006/0171991 A1 | 8/2006 | Bango | |
| 2006/0246113 A1 | 11/2006 | Griffith et al. | |
| 2008/0002149 A1 | 1/2008 | Fritsch et al. | |
| 2009/0060961 A1 * | 3/2009 | Naruse | A61K 8/02 424/401 |
| 2009/0217849 A1 | 9/2009 | Eastin et al. | |
| 2009/0238858 A1 | 9/2009 | Kohn et al. | |
| 2010/0285094 A1 | 11/2010 | Gupta | |
| 2011/0217355 A1 * | 9/2011 | Chauhan | A61K 9/0051 424/429 |
| 2011/0230589 A1 * | 9/2011 | Maggio | C07F 7/0854 523/107 |
| 2012/0116019 A1 | 5/2012 | Suzuki et al. | |
| 2013/0131214 A1 | 5/2013 | Scales et al. | |

OTHER PUBLICATIONS

Kenawy, E., et al., "Controlled Release of Ketoprofen From Eletrospun Poly(vinyl alcohol) Nanofibers," Materials Science and Engineering A 459 pp. 390-396, 2007.
Huang, Z, et al., "A Review on Polymer Nanofibers by Electrospinning and Their Applications in Nanocomposites," Composites Science and Technology 63, pp. 2223-2253, 2003.
PCT Patent Application PCT/US2010/029126 International Search Report and Written Opinion, dated Jan. 14, 2011, 11 pages.
U.S. Appl. No. 12/416,802 Select File History dated Sep. 17, 2010 through Aug. 22, 2011, 43 pages.
European Patent Application 10764841.2 Search Report dated Sep. 17, 2013, 20 pages.
Tauber, S., et al. "Polymer Electrospinning as a Novel Technique to Create a PVA Contact Lens," Retrieved from the Internet: URL:http://ascrs2008.abstractsnet.com/handouts/00194_040508_TBA_0800_Tauber_Sachar.ppt, Apr. 2008.
(Continued)

*Primary Examiner* — Audrea Buckley
(74) *Attorney, Agent, or Firm* — Polsinelli PC

(57) ABSTRACT

Contact lenses are described that include particles of polymer fiber mat incorporated into a polymer lens wherein the polymer fiber mat is formed by electrospinning a prepolymer solution. Methods for making the contact lenses with improved oxygen permeability are also described. Methods for making the contact lens with optional therapeutic drug delivery and refractive correction are also described.

40 Claims, 5 Drawing Sheets

(56) References Cited

OTHER PUBLICATIONS

Davis, G.E., et al., "Electrospun Polymers 1-5, 16 in Cornea Repair and Regeneration," Annual ARVO Meeting Retrieved from Internet: URL:http://files.abstractsonline.com/SUPT/163/1808/NT%20Section.pdf., Apr. 2008
Sith, M.E., et al., "Incorporation and Release of Immunoglobulin G as a Model Protein System From Biphasic Polymeric Tissue Engineering Scaffolds Produced Through Electrospinning," Annual ARVO meeting, Retrieved from Internete: URL:http://files.abstractsonline.com/SUPT/163/1808/NT%Section.pdf, Apr. 2008.
PCT Patent Application PCT/US14/43239 International Search Report and Written Opinion dated Nov. 14, 2014, pp. 13.
Ji, et al, "Fluorination of Electrospun Hydrogel Fibers for a Controlled Release Drug Delivery System," ACTA Biomaterialia, vol. 6, No. 1, pp. 102-109, Jun. 14, 2009.
U.S. Appl. No. 12/490,972, select file history dated Jun. 30, 2011 through Sep. 25, 2012, 87 pages.

\* cited by examiner

EXTENDED RELEASE DRUG-DELIVERY CONTACT LENSES AND METHODS OF MAKING

CROSS-REFERENCE TO RELATED APPLICATIONS

This application claims the benefit of U.S. Patent Application Ser. No. 61/837,537 filed Jun. 20, 2013 and U.S. Patent Application Ser. No. 61/837,530 filed Jun. 20, 2013, the disclosures of which are incorporated herein by reference.

BACKGROUND

While significant advances have been achieved in the field of contact lens design and fabrication, many problems still exist. Paramount of these is the fact that it is common for a contact lens to be constructed as a completely homogenous solid or with a homogenous outer surface enclosing a hydrogel or polymeric interior, which means that the lens outer covering material is consistent throughout its structure. These structures reduce the available oxygen to the corneal surface, minimize tear and aqueous transport through the lens, and act as a nucleation point for protein buildup.

Electrospun polymer fibers provide a material with a variety of favorable characteristics that may be tailored to fit various applications. It is therefore desirable to provide an ophthalmic drug delivery system utilizing electrospun polymer fibers. The system may utilize an improved contact lens incorporating electrospun fibers with desired characteristics, and a system and method for delivering ophthalmic drugs from the improved contact lens to an eye over an extended period of time while maintaining the concentration of the drug in the eye at an efficacious level throughout the period of drug delivery.

A number of patents disclose the use of electrospun fibers for ocular adaptation or treatment. For example, U.S. Pat. No. 7,563,396 discloses a technique for creating polymer fibril diameters and spacing that duplicate the optical transmission and diffusion characteristics of natural corneal collagen; U.S. Pat. No. 8,083,347 discloses methods of coating and cross-linking polymer fibers in contact lenses; and U.S. Pat. No. 8,361,492 discloses drug-delivery systems, both through direct use of electrospun fibers in the eye and by inclusion of the fibers in a contact lens.

SUMMARY

The disclosed methods enable the manufacture of contact lenses that have high oxygen permeability, while allowing the option of having either a lipid impermeable or lipid permeable functionality. This functionality is of great importance in designing a therapeutic contact lens, in addition to a refractive contact lens. In either case, a high degree of oxygen permeability is desired as the cornea is an avascular membrane that receives its oxygen supply directly through the air. Any obstruction of the corneal surface's direct contact with the surrounding air is considered detrimental.

The disclosed devices and methods overcome many of the limitations inherent in current contact lens design and production including: (a) providing means of producing contact lenses that exhibit the optical and diffusive characteristics of natural corneal tissue, (b) providing a scaffold lens structure that can permit the absorption or adsorption of specific chemical species for the purpose of drug delivery to treat specific eye conditions, (c) providing a scaffold lens structure that can permit the absorption or adsorption of specific chemical species for the purpose of minimizing or eliminating protein deposits, (d) reducing or eliminating corneal dry eye condition by permitting increased diffusion of tear fluids and by delivering selected compounds to natural tear components, (e) producing a viable collagen polymer refractive correcting contact lens whose characteristics duplicate natural tissue, (f) promoting corneal health and reducing the possibility of conventional lens-caused infections since the diffusive characteristics promote anti-microbial agent distribution natural to the eye, (g) reducing abnormal blood vessel in growth which occurs when long term contact lens wear reduces the average oxygen transport to the corneal surface, (h) providing a scaffold lens structure that can permit the absorption or adsorption of various chemical species for the purposes of drug delivery to precise portions of the cornea, thereby keeping a regulated, time lapsed drug delivery confined to not only the cornea, but specific regions of the cornea, and (i) manufacturing a contact lens with the ability to control the location and the amount of surface hydrophobicity and hydrophilicity tailored to the application, as required.

A process known as "electrospinning" is used to produce a permeable contact lens composed of micro strands that approximate the nanometer size fibrils of natural human corneal stromal collagen. The fibril diameter is regarded as the principal factor in achieving corneal transparency. The fibril strands are deposited onto an appropriate target, which allows a suitable polymer fibril scaffold "mat" to develop. The density and configuration of this "mat" determine the permeability of the structure to aqueous fluids, lipids, and gases. The density and orientation of these fibrils can be controlled in order to achieve the desired diffusive and optical parameters compatible with natural tissue.

The drug delivery system described herein utilizes both "raw" electrospun fibers and an improved contact lens as the means of drug delivery. The fibers and the improved contact lens provide a drug delivery system comprising a drug-releasing scaffold formed from a mat of electrospun fibers and methods for incorporating various therapeutic drugs into the mat. The fiber mat may be utilized directly in the eye for delivery of drugs, or incorporated into an improved contact lens.

The therapeutic drugs may be loaded into the drug delivery system by soaking the electrospun mats in a solution containing the drug, or by providing the drugs in the solution feeding the electrospinning process thus incorporating the drug into the fibers in the electrospun mat. Various processes for treating the electrospun mats after loading with therapeutic drugs are also described for improving the drug delivery characteristics, such as coating the mats in a polymer and cross-linking the electrospun fibers.

The improved contact lens described herein also comprises a contact lens that incorporates electrospun fibers to provide desirable physical characteristics. The improved contact lens may be fabricated with a thinner cross-section due to the increased mechanical strength and rigidity of the electrospun fiber materials. The thinner cross-section lens provides increased oxygen permeability while maintaining mechanical strength.

In an aspect, a method for forming a contact lens comprises the steps of: electrospinning a mat of polymer fibers; providing a therapeutic drug in or on the polymer fibers; processing the mat of polymer fibers comprising a therapeutic drug to form a plurality of particles; isolating particles having dimensions less than or equal to 500 micrometers; and incorporating the isolated particles into a contact lens.

In one embodiment, the step of processing the mat of polymer fibers comprising the therapeutic drug to form the plurality of particles comprises grinding, cutting, tearing, chipping, pulverizing, milling or a combination thereof.

In one embodiment, the step of isolating particles comprises sieving, gravity separation, electrostatic separation or combinations thereof. For example, the isolated particles may have dimensions less than or equal to 500 micrometers, or less than or equal to 300 micrometers, or less than or equal to 100 micrometers. In an embodiment, the isolated particles may have dimensions selected from the range of 100 micrometers to 500 micrometers or selected from the range of 100 micrometers to 300 micrometers.

In one embodiment, the step of providing the therapeutic drug in or on the polymer fibers comprises soaking the fibers in a solution containing the therapeutic drug. In another embodiment, the step of providing the therapeutic drug in or on the polymer fibers comprises spinning the fibers from a solution containing the therapeutic drug. For example, the solution may contain between 5 and 25 percent polymer by weight and/or the concentration of the therapeutic drug in the solution may be between 0.01% and 25%.

In one embodiment, the method further comprises a step of adding a therapeutic drug to a polymer lens formulation either before the lens is formed or by soaking the formed contact lens in a solution containing a therapeutic drug. For example, the concentration of the therapeutic drug in the solution may be between 0.01% and 25%.

In an aspect, a drug delivery system comprises: a contact lens comprising electrospun fibers incorporated into a polymer lens, wherein the electrospun fibers comprise a therapeutic drug, and wherein the fibers are processed into particles having dimensions less than or equal to 500 micrometers, or less than or equal to 300 micrometers, or less than or equal to 100 micrometers. In an embodiment, the particles have dimensions selected from the range of 100 micrometers to 500 micrometers or selected from the range of 100 micrometers to 300 micrometers.

In an embodiment, a concentration of the particles in the contact lens may be between 0.01 percent by weight and 50 percent by weight, or between 0.05 percent and 30 percent, or between 1 percent and 15 percent, or between 2 percent and 10 percent. In an embodiment, a concentration of the particles in the contact lens may be at least 0.01 percent by weight, or at least 0.05 percent, or at least 1 percent, or at least 2 percent, or at least 5 percent. In an embodiment, the particles and the polymer lens material are present in the contact lens with a weight ratio between 1:10,000 and 1:2, or between 1:1,000 and 1:2, or between 1:250 and 1:3, or between 1:50 and 1:3, or between 1:10 and 1:2.

In an embodiment, the particles are at least 90% transparent to electromagnetic energy in the visible range of the electromagnetic spectrum.

In an embodiment, the contact lens has a shape that provides refractive correction. In an alternate embodiment, the contact lens has a shape that does not provide refractive correction. In an embodiment, the lens is a corneal lens or a scleral lens.

In an embodiment, the contact lens has a thickness selected from the range of 0.01 mm to 0.5 mm and a Young's modulus selected from the range of 0.25 MPa to 0.60 MPa. In other embodiments, the contact lens has a Young's modulus in the range of 0.10 MPa to 0.80 MPa. In other embodiments, the contact lens may have a Young's modulus outside the above-mentioned ranges.

In an embodiment, the therapeutic drug is eluted from the particles in situ for a period of at least 3 days, or for a period of at least 5 days, or for a period of at least 7 days. In an embodiment, the therapeutic drug is eluted from the particles in situ for a period selected from the range of 1 day to 7 days, or for a period selected from the range of 1 day to 5 days, or for a period of 1 day to 3 days.

In an embodiment, a method for forming a contact lens may further comprise a step of applying a cross-linking treatment to the mat of polymer fibers. For example, the cross-linking treatment may include cross-linking via reaction with methanol.

In an embodiment, a method for forming a contact lens may further comprise a step of cooling the mat of polymer fibers prior to the step of processing the mat to form a plurality of particles. For example, the cooling step may comprise mechanical cooling and/or exposing the mat of polymer fibers to a cooling agent selected from the group consisting of liquid nitrogen, liquid helium, a dry ice bath, and combinations thereof.

In an embodiment, the polymer forming the mat and or the polymer of the contact lens is selected from the group consisting of poly(2-hydroxyethylmethacrylate), poly(acrylic acid), poly(methacrylic acid), poly(vinyl pyrrolidone), poly(N-vinyl pyrrolidone), poly(vinyl alcohol), poly(methyl methacrylate), poly(glycerol methacrylate), silicone hydrogels, fluorocarbon hydrogels, polyacrylamide, polymers of silicone, polymers of (3-methacryloxy-2-hydroxypropyloxy)propyl-bis(trimethylsiloxy)methylsilan-e, polymers of $C_3$-$C_{18}$ alkyl and $C_3$-$C_{18}$ cycloalkyl acrylates and methacrylates, polymers of $C_3$-$C_{18}$ alkylacrylamides and -methacrylamides, polyacrylonitrile, polymethacrylonitrile, polymers of vinyl $C_1$-$C_{18}$ alkanoates, polymers of $C_2$-$C_{18}$ alkenes, polymers of $C_2$-$C_{18}$ haloalkenes, polystyrene, poly-lower alkyl styrene, polymers of lower alkyl vinyl ethers, polymers of $C_2$-$C_{10}$ perfluoroalkyl acrylates and methacrylates or correspondingly partly fluorinated acrylates and methacrylates, polymers of $C_3$-$C_{12}$ perfluoroalkyl-ethyl-thiocarbonylaminoethyl acrylates and methacrylates, polymers of acryloxy- and methacryloxy-alkylsiloxanes, poly(N-vinylcarbazole), polymers of $C_1$-$C_{12}$ alkyl esters of maleic acid, poly(fumaric acid), poly(itaconic acid), poly(mesaconic acid), polymers of $C_1$-$C_4$ alkyl esters of vinylically unsaturated carboxylic acids having 3 to 5 carbon atoms, polymers of vinyl esters of carboxylic acids having up to 5 carbon atoms, poly(methyl acrylate), poly(ethyl acrylate), poly(propyl acrylate), poly(isopropyl acrylate), poly(isobutyl acrylate), poly(isooctyl acrylate), poly(isodecyl acrylate), poly(cyclohexyl acrylate), poly(2-ethylhexyl acrylate), poly(ethyl methacrylate), poly(propyl methacrylate), poly(butyl acrylate), poly(vinyl acetate), poly(vinyl propionate), poly(vinyl butyrate), poly(vinyl valerate), poly(chloroprene), poly(vinyl chloride), poly(vinylidene chloride), polymers of 1-butene, polybutadiene, poly(vinyl toluene), poly(vinyl ethyl ether), polymers of perfluorohexylethylthiocarbonylaminoethyl methacrylate, poly(isobornyl methacrylate), polymers of trifluoroethyl methacrylate, polymers of hexafluoroisopropyl methacrylate, polymers of hexafluorobutyl acrylate, polymers of hexafluorobutyl methacrylate, polymers of tris-trimethylsilyloxy-silyl-propyl methacrylate, polymers of 3-methacryloxypropylpentamethyldisiloxane, polymers of bis(methacryloxypropyl)tetramethyldisiloxane, polymers of hydroxyl-substituted lower alkyl acrylates and methacrylates, polymers of lower alkylacrylamides and -methacrylamides, polymers of ethoxylated acrylates and methacrylates, polymers of hydroxyl-substituted lower alkylacrylamides and -methacrylamides, polymers of hydroxyl-substituted lower alkyl vinyl ethers, poly(sodium vinylsulfonate), poly(sodium styrenesulfonate), polymers of 2-acrylamido-2-methylpropanesulfonic acid, poly(N-vinylpyrrole), poly(N-vinyl-2-pyrrolidone), polymers of 2-vinyloxazoline, polymers of 2-vinyl-4,4'-dialkyloxazolin-5-one, poly(2-vinylpyridine), poly(4-vinylpyridine), polymers of vinylically unsaturated carboxylic acids having a total of 3 to 5 carbon atoms, polymers of amino-lower alkyl (where the term "amino" also includes quaternary ammonium), polymers of mono-lower alkylamino-lower alkyl and di-lower alkylamino-lower alkyl acrylates and methacrylates, poly(allyl alcohol), polymethacrylamide, polymers of hydroxyl-substituted lower alkyl acrylates and methacrylates, hydroxyethyl methacrylate, poly(hydroxyethyl acrylate), poly(hydroxypropyl acrylate), poly(dimethylaminoethyl methacrylamide), poly(ynylpyridine), poly(glycerol methacrylate), polymers of N-(1,1-dimethyl-3-oxobutyl) acrylamide, poly(dimethylaminoethyl methacrylate), polymers of trimethylammonium-2-hydroxypropyl methacrylate hydrochloride, poly(N,N-di methylacrylamide), hydroxyl-functional polymers including poly(ethylene vinyl alcohol) copolymer (PEVOH), poly(propylene vinyl alcohol) copolymer (PPVOH), PVA (poly vinyl alcohol), PPA (polypropylene alcohol), and other co-polymers containing free hydroxyl groups, and mixtures thereof.

In an embodiment, the therapeutic drug is selected from the group consisting of antibacterial antibiotic drugs, synthetic antibacterial drugs, antifungal antibiotic drugs, synthetic antifungal drugs, antineoplastic agents, steroidal anti-inflammatory agents, non-steroidal anti-inflammatory agents, anti-allergic agents, glaucoma-treating agents, antiviral agents and anti-mycotic agents.

In an aspect, a contact lens comprises particles of polymer fiber mat incorporated into a polymer lens, wherein the polymer fibers of the mat have diameters selected from the range of 2 micrometers to 1 nanometer, and wherein the particles of polymer fiber mat have dimensions less than or equal to 500 micrometers, or less than or equal to 300 micrometers, or less than or equal to 100 micrometers.

In an embodiment, a contact lens has a thickness selected from the range of 0.01 mm to 0.5 mm and an oxygen permeability selected from the range of 15E-11 Dk to 75E-11 Dk.

In an embodiment, a contact lens has a thickness selected from the range of 0.01 mm to 0.5 mm and a Young's modulus selected from the range of 0.25 MPa to 0.60 MPa.

In an embodiment, the particles are ground, electrospun polymer fibers.

In an aspect, a method for forming a contact lens comprises the steps of: providing particles of polymer fiber mat, wherein the polymer fibers of the mat have diameters selected from the range of 2 micrometers to 1 nanometer, and wherein the particles of polymer fiber mat have dimensions less than or equal to 500 micrometers; and incorporating the particles into a polymer lens.

In an embodiment, the method further comprises a step of shaping the contact lens by lathe cutting, molding, laser ablating or a combination thereof.

In an embodiment, the step of providing particles of polymer fiber mat includes electrospinning a mat of polymer fibers; processing the mat of polymer fibers to form a plurality of particles; and isolating particles having dimensions less than or equal to 500 micrometers, or less than or equal to 300 micrometers, or less than or equal to 100 micrometers.

In an embodiment, the step of processing the mat of polymer fibers to form the plurality of particles comprises grinding, cutting, tearing, chipping, pulverizing, milling or a combination thereof.

In an embodiment, the step of isolating particles comprises sieving, gravity separation, electrostatic separation or combinations thereof.

DETAILED DESCRIPTION

Figure 1:
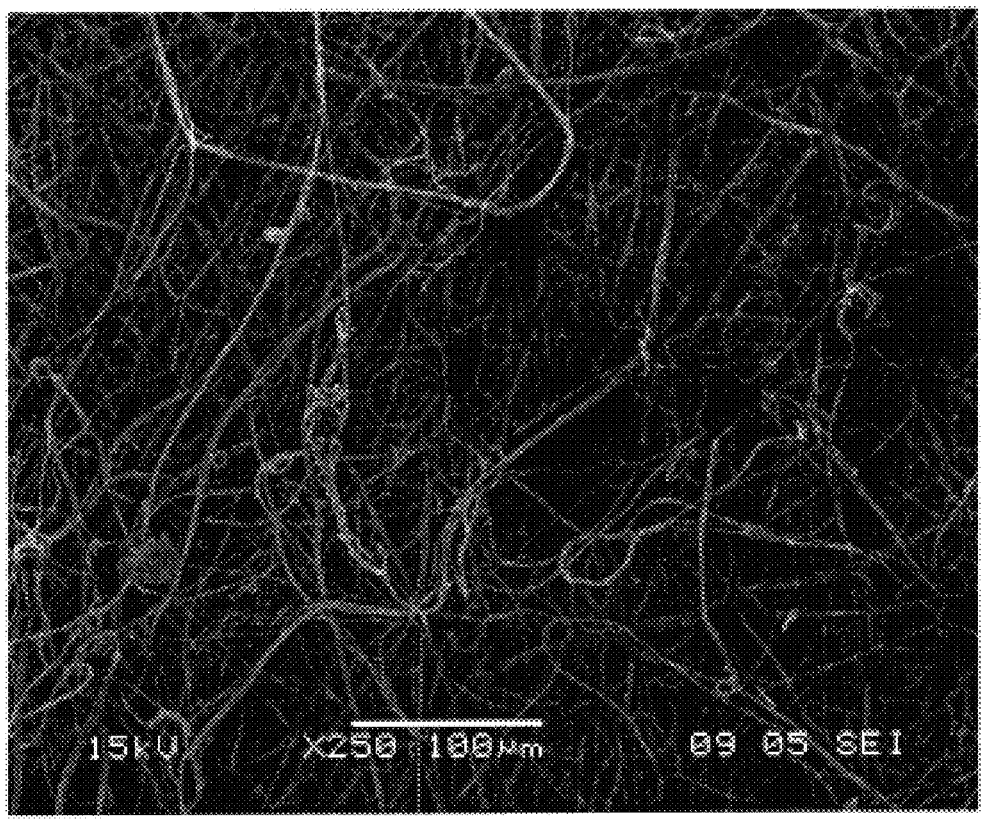
FIG. 1 is a scanning electron micrograph of a fiber mat created by electrospinning poly(vinyl alcohol). The fibers are deposited randomly throughout the mat in various orientations.
Figure 2:
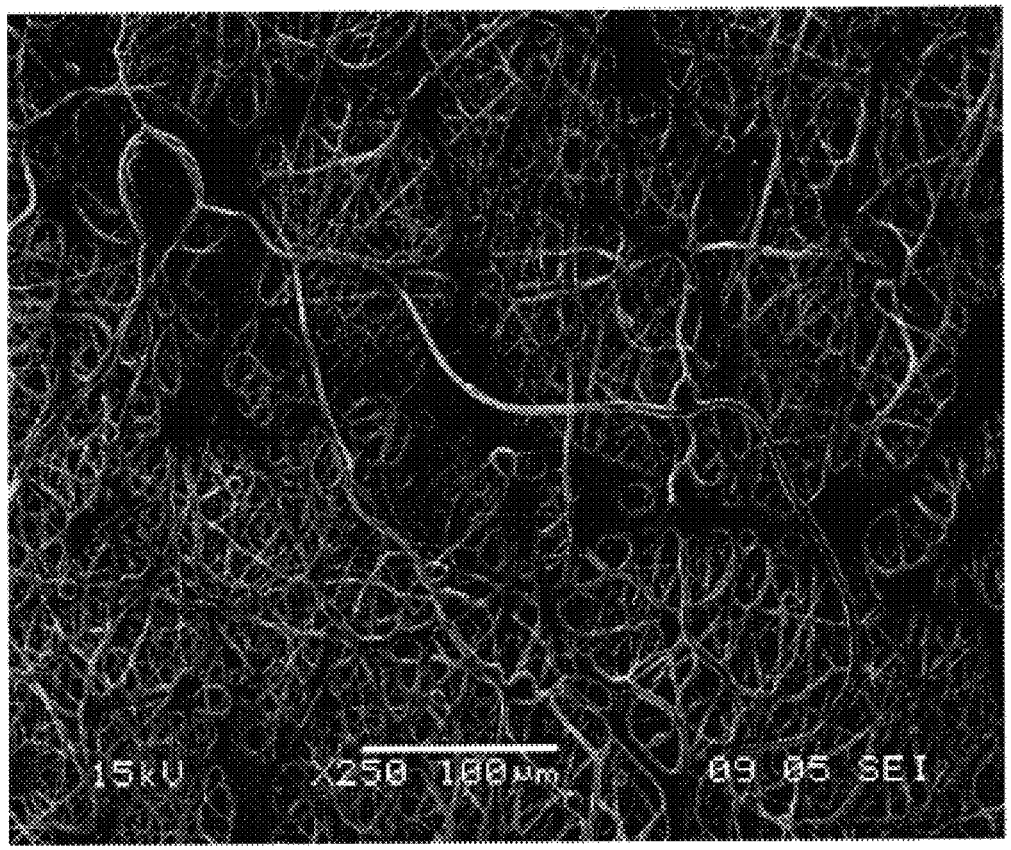
FIG. 2 is a scanning electron micrograph of a fiber mat created by electrospinning poly(vinyl alcohol) and cross-linking the resulting mat using methanol as a crosslinking agent. As can be seen in the figure, the fibers are linked at the intersection of overlapping fibers.

In general, the terms and phrases used herein have their art-recognized meaning, which can be found by reference to standard texts, journal references and contexts known to those skilled in the art. The following definitions are provided to clarify their specific use in the context of this description.

The terms "embedded" or "encapsulated" refer to the orientation of one structure such that it is at least partially, and in some cases completely, surrounded by one or more other structures. "Partially embedded" or "partially encapsulated" refer to the orientation of one structure such that it is partially surrounded by one or more other structures, for example, wherein 30%, or optionally 50%, or optionally 90%, of the external surfaces of the structure is surrounded by one or more structures. "Completely embedded" or "completely encapsulated" refers to the orientation of one structure such that it is completely surrounded by one or more other structures.

The terms "direct" and "indirect" describe the actions or physical positions of one component or layer relative to another component or layer, or one device relative to another device. For example, a component or layer that "directly" acts upon or touches another component or layer does so without intervention from an intermediary. Contrarily, a component or layer that "indirectly" acts upon or touches another component or layer does so through an intermediary (e.g., a third component).

"Contiguous" refers to materials or layers that are touching or connected throughout in an unbroken sequence.

"Polymer" refers to a macromolecule composed of repeating structural units connected by covalent chemical bonds or the polymerization product of one or more monomers, often characterized by a high molecular weight. The term polymer includes homopolymers, or polymers consisting essentially of a single repeating monomer subunit. The term polymer also includes copolymers, or polymers consisting essentially of two or more monomer subunits, such as random, block, alternating, segmented, grafted, tapered and other copolymers. Crosslinked polymers having linked monomer chains are particularly useful for some applications.

"Young's modulus" is a mechanical property of a material, device or layer which refers to the ratio of stress to strain for a given substance. Young's modulus may be provided by the expression:

$$E = \frac{(\text{stress})}{(\text{strain})} = \left(\frac{L_0}{\Delta L}\right)\left(\frac{F}{A}\right), \quad (I)$$

where E is Young's modulus, $L_0$ is the equilibrium length, $\Delta L$ is the length change under the applied stress, F is the force applied, and A is the area over which the force is applied. Young's modulus may also be expressed in terms of Lame constants via the equation:

$$E = \frac{\mu(3\lambda + 2\mu)}{\lambda + \mu}, \quad (II)$$

where $\lambda$ and $\mu$ are Lame constants.

"Bending stiffness" is a mechanical property of a material, device or layer describing the resistance of the material, device or layer to an applied bending moment. Generally, bending stiffness is defined as the product of the modulus and area moment of inertia of the material, device or layer. A material having an inhomogeneous bending stiffness may optionally be described in terms of a "bulk" or "average" bending stiffness for the entire layer of material.

Electrospun Fiber Mat Fabrication

The electrospun fiber mat used in the present invention is fabricated by electrospinning polymer solution and loading a therapeutic drug in the fiber mat using a variety of techniques, which are described below with examples.

The electrospinning process typically comprises an apparatus including one or more electrically-conducting liquid dispensers, such as a stainless steel needle, disposed adjacent to a collector. The liquid dispenser is held at a high electric potential, or voltage, with respect to the collector. The electric potential may be either alternating current (AC) or direct current (DC), or a DC biased AC voltage. Alternatively, a substrate for receiving the electrospun fibers may be inserted between the conducting dispenser and the collector such that the fibers will be deposited on the substrate as they are propelled from the liquid dispenser by the electric field toward the collector.

A solution source, or well, containing a solution of the polymer and various other components which may include a polymer precursor (monomer) is attached to the electrically-conducting liquid dispenser by a fluid conducting element such as a short tube. The polymer solution is propelled through the dispenser at a predetermined rate, either by gravity or by mechanical means such as a pump. As the solution is dispensed through the electrically-conducting dispenser, the high electric potential between the dispenser and the collector leads to the formation of uniform fibers which are deposited on the collector. The fibers may be micro-fibers or nano-fibers depending on the parameters of the electrospinning process. As the fibers are deposited on the collector they overlap to form a mat, as further described below.

Polymer solutions for use in the fiber mat fabrication disclosed herein include, but are not limited to, solutions having between 5 and 25 percent polymer by weight. Suitable solvents for the polymer solutions include, for example, water, alcohols and FDA class III organic solvents. Various additives may be added to the precursor solution to lower surface tension, or to otherwise alter the characteristics of the solution or the electrospun fibers as desired. For example, surfactants, such as Triton X-100, poloxomer 407 or other suitable surfactant, may be added to the precursor solution to lower the surface tension of the solution.

Polymers for use in the electrospinning process include, but are not limited to the following: poly(2-hydroxyethyl-methacrylate) (pHEMA), poly(acrylic acid) (PAA), poly (methacrylic acid), poly(vinyl pyrolidone) (PVP), poly(N-vinyl pyrolidone) (PVP), polyvinyl alcohol (PVA), poly (methyl methacylate) (PMMA), poly(glyceral methacrylate) (PGMA), silicone hydrogels, fluorocarbon hydrogels, polyacrylamide (PAM), polyethylene glycol (PEG), polycaprolactone (PCL), poly(lactic-co-glycolic acid) (PLGA), polyvinyl alcohol (PVA), silicone and 3-methacryloxy-2 hydroxypropyloxy)propylbis(trimethylsiloxy)methylsilane. Other polymers may be utilized if soluble in a solvent such as water, methanol, ethanol, hexane, acetonitrile, or tetrahydrofuran to allow the electrospinning process. Additional polymer precursor solutions are described below.

As the fibers are deposited on the collector they form a mat of overlaying fibers. In some methods of depositing the fibers, the collector is translated in one or more linear dimensions, or in a rotational or orbital manner, perpendicular to the direction of fiber deposition to increase the area over which the fibers are deposited and to improve the consistency of the fiber mat.

After a desired period of deposition, a fiber mat of a certain thickness will be formed, and can be removed from the electrospinning apparatus and prepared for further processing.

After deposition, the fiber mat may be processed in several ways to improve the characteristics of the fiber mat. The fiber mat may be coated with a polymer by exposing the mat to a solution of polymer precursor. As described below, coating the fiber mat alters the characteristics of the fiber mat, including the release of drugs incorporated in the fiber mat. After any chemical processing, the mats may be further processed by cutting into sections or grinding into particles.

The fiber mats may also be processed by exposing them to a crosslinking agent such as ethylene glycol dimethacrylate (EGDMA), tetraethylene glycol dimethacrylate (TEGDMA), divinyl benzene (DVB), divinylacrylamide (DVACR), or any tri-allyl crosslinking agent when there is at least one active alkene in the chain. Methanol may be added to PVA to crosslink the polymer. The crosslinking process increases the mechanical stability of the fiber mat by linking adjacent fibers as they intersect randomly in the fiber mat.

An example process for creating an electrospun fiber mat is as follows. 1. Combine the following materials, mix, place over heat and stir inside round-bottom flask with attached condenser for 6.5 hours. 10 wt % PPVA+2 wt Triton X-100+DI water 11.363 g Polyvinyl alcohol (Sigma-Aldrich 99% hydrolyzed) 2.277 g Triton X-100 (Aldrich) 27.539 g Ultra high purified water added to Triton X-100 (Elgan) 72.459 g Ultra high purified water added to PVA (Elgan). This is the PVA polymer mixture. Without allowing the polymer mixture to cool, performing the following steps. 2. Add 2.000 ml of Vigamox to 14.141 g of the PVA polymer mixture and vortex stir for 1 minute. 3. Add 7.0 ml of the PVA/Vigamox solution to 2 syringes for a total of 14.0 ml of solution. 4. Electrospin the PVA/Vigamox solution from both needles simultaneously at the following parameters: Dispense rate: 1.8 ml/hr 18 gauge blunt end needles Voltage: 30 kV Travel distance: 4 in Total time: 2.5 hours 5. After electrospinning, the resulting mat is cut into approximately 3.0 mg squares. 6. If crosslinking is desired, soak the squares in methanol for 7 hours and allow to air dry in ambient conditions overnight. 7. Coat the squares in the remaining PVA polymer solution created in step 1 above. Before coating the squares, the PVA polymer solution is heated in a round bottom flask with attached condenser for 2 hours. 8. After coating the squares in the polymer solution, allow them to air dry in ambient conditions overnight. 9. If a second cross-link is desired soak the squares in methanol for 7 hours and then allow them to air dry in ambient conditions overnight.

When measuring drug release profiles the following procedure was utilized: 1. Each sample mat was placed into 0.5 ml ISO 18369 saline solution in cuvettes. 2. Absorbance measurements were taken at 1, 5, 10, 20, 60, 1440, and 2880 minutes by removing the sample mat with tweezers and measuring the absorbance at an appropriate wavelength for the drug of interest. Sample mats were immediately placed back in the sample cuvette after measurement 3. Measurements were normalized by mass of the sample mat prior to dip-coating by measuring hydration parameters on the polymerized materials.

Polymer Materials for Electrospun Fibers

Suitable hydrophobic comonomers (a) for use in electrospun fibers include, without this list being exhaustive, $C_1$-$C_{18}$ alkyl and $C_3$-$C_{18}$ cycloalkyl acrylates and methacrylates, $C_3$-$C_{18}$ alkylacrylamides and -methacrylamides, acrylonitrile, methacrylonitrile, vinyl $C_1$-$C_{18}$ alkanoates, $C_6$-$C_{18}$ alkenes, $C_2$-$C_{18}$ haloalkenes, styrene, lower alkyl styrene, lower alkyl vinyl ethers, $C_2$-$C_{10}$ perfluoroalkyl acrylates and methacrylates or correspondingly partly fluorinated acrylates and methacrylates, $C_3$-$C_{12}$ perfluoroalkyl-ethyl-thio-carbonylaminoethyl acrylates and methacrylates, acryloxy- and methacryloxy-alkylsiloxanes, N-vinylcarbazole and $C_1$-$C_{12}$ alkyl esters of maleic acid, fumaric acid, itaconic acid, mesaconic acid and the like. Preferred comonomers are, for example, acrylonitrile, $C_1$-$C_4$ alkyl esters of vinylically unsaturated carboxylic acids having 3 to 5 carbon atoms, or vinyl esters of carboxylic acids having up to 5 carbon atoms.

Examples of suitable hydrophobic comonomers (a) include methyl acrylate, ethyl acrylate, propyl acrylate, isopropyl acrylate, isobutyl acrylate (IBA), isooctyl acrylate (OA), isodecyl acrylate (DA), cyclohexyl acrylate, 2-ethylhexyl acrylate (EHA), methyl methacrylate, ethyl methacrylate, propyl methacrylate, butyl acrylate, vinyl acetate, vinyl propionate, vinyl butyrate, vinyl valerate, styrene, chloroprene, vinyl chloride, vinylidene chloride, acrylonitrile, 1-butene, butadiene, methacrylonitrile, vinyl toluene, vinyl ethyl ether, perfluorohexylethylthiocarbonylaminoethyl methacrylate, isobornyl methacrylate, trifluoroethyl methacrylate, hexafluoroisopropyl methacrylate, hexafluorobutyl (meth)acrylate (HFBMA and HFBA), tris-trimethylsilyloxy-silyl-propyl methacrylate (TRIS), 3-methacryloxypropyl-pentamethyldisiloxane and bis(methacryloxypropyl) tetramethyldisiloxane. Preferred examples of hydrophobic comonomers (a) are methyl methacrylate, IBA, HFBA, HFBMA, OA, EHA, DA, TRIS and acrylonitrile. Suitable hydrophilic comonomers (a) include, without this list being conclusive, hydroxyl-substituted lower alkyl acrylates and methacrylates, acrylamide, methacrylamide, lower alkylacrylamides and -methacrylamides, ethoxylated acrylates and methacrylates, hydroxyl-substituted lower alkylacrylamides and -methacrylamides, hydroxyl-substituted lower alkyl vinyl ethers, sodium vinylsulfonate, sodium styrene-sulfonate, 2-acrylamido-2-methylpropanesulfonic acid, N-vinylpyrrole, N-vinyl-2-pyrrolidone, 2-vinyloxazoline, 2-vinyl-4,4'-dialkyloxazolin-5-one, 2- and 4-vinylpyridine, vinylically unsaturated carboxylic acids having a total of 3 to 5 carbon atoms, amino-lower alkyl (where the term "amino" also includes quaternary ammonium), mono-lower alkylamino-lower alkyl and di-lower alkylamino-lower alkyl acrylates and methacrylates, allyl alcohol and the like. Preferred comonomers are, for example, N-vinyl-2-pyrrolidone, acrylamide, methacrylamide, hydroxyl-substituted lower alkyl acrylates and methacrylates, hydroxyl-substituted lower alkylacrylamides and -methacrylamides and vinylically unsaturated carboxylic acids having a total of 3 to 5 carbon atoms. Examples of suitable hydrophilic comonomers (a) include hydroxyethyl methacrylate (HEMA), hydroxyethyl acrylate, hydroxypropyl acrylate, trimethylammonium-2-hydroxy-ypropyl methacrylate hydrochloride (Blemer® MQA, for example from Nippon Oil), dimethylaminoethyl meth acrylate (DMAEMA), dimethylaminoethyl methacrylamide, acrylamide, methacrylamide, N,N-dimethylacrylamide (DMA), allyl alcohol, vinylpyridine, glycerol methacrylate, N-(1,1-dimethyl-3-oxobutyl)acrylamide, N-vinyl-2-pyrrolidone (NVP), acrylic acid, methacrylic acid and the like. Preferred hydrophilic comonomers (a) are 2-hydroxyethyl methacrylate, dimethylaminoethyl methacrylate, trimethylammonium-2-hydroxypropyl methacrylate hydrochloride, N,N-dimethyl-acrylamide and N-vinyl-2-pyrrolidone.

The polymers according to the invention are built up in a known manner from the corresponding monomers (the term monomers here also including a macromer according to the invention) by a polymerization reaction with which the expert is familiar. Usually, a mixture of the above-mentioned monomers is heated, with the addition of an agent which forms free radicals. Such an agent which forms free radicals is, for example, azoisobutyronitrile (AIBN), potassium peroxodisulfate, dibenzoyl peroxide, hydrogen peroxide or sodium percarbonate. If the compounds mentioned are heated, for example, free radicals are then formed, by homolysis, and can then, for example, initiate a polymerization.

A polymerization reaction can be carried out using a photoinitiator. Photopolymerization is the term used in this case. For photopolymerization, a photoinitiator which can initiate free radical polymerization and/or crosslinking by the use of light is suitably added. Examples of this are familiar to the expert, and specifically, suitable photoinitiators are benzoin methyl ether, I-hydroxycyclohexyl phenyl ketone and Darocur and Irgacur types, preferably Darocur 11738® and Darocur 29590®. Reactive photoinitiators which can be incorporated, for example, into a macromer or can be used as a special comonomer (a) are also suitable. Examples of these are to be found in EP 632 329. The photopolymerization can then be triggered by actinic radiation, for example light, in particular UV light of a suitable wavelength. The spectral requirements can be controlled accordingly, if appropriate, by addition of suitable photosensitizers. Polymerization can be carried out in the presence or absence of a solvent. Suitable solvents are in principle all solvents which dissolve the monomers used, for example water, alcohols, such as lower alkanols, for example ethanol or methanol, and furthermore carboxylic acid amides, such as dimethylformamide, dipolar aprotic solvents, such as di methyl sulfoxide or methyl ethyl ketone, ketones, for example acetone or cyclohexanone, hydrocarbons, for example toluene, ethers, for example THF, dimethoxyethane or dioxane, and halogenated hydrocarbons, for example trichloroethane, and also mixtures of suitable solvents, for example mixtures of water with an alcohol, for example a water/ethanol or a water/methanol mixture.

If appropriate, a polymer network can be intensified by addition of a so-called crosslinking agent, for example a polyunsaturated comonomer (b). The invention furthermore relates to a polymer comprising the polymerization product of a macromer according to the invention with, if appropriate, at least one vinylic comonomer (a) and with at least one comonomer (b). Examples of typical comonomers (b) are, for example, allyl(meth)acrylate, lower alkylene glycol di(meth)acrylate, poly lower alkylene glycol di(meth)acrylate, lower alkylene di(meth)acrylate, divinyl ether, divinyl sulfone, di- or trivinylbenzene, trimethylolpropane tri(meth)acrylate, pentaerythritol tetra(meth)acrylate, bisphenol A di(meth)acrylate, methylenebis(meth)acrylamide, triallyl phthalate or diallyl phthalate.

TABLE 1

| Monomer/Cat/Crosslinker | % | % | % | % | % | % |
|---|---|---|---|---|---|---|
| MMA | 25.5 | | | 24.2 | | |
| GMA | 68 | | | | | |
| HEMA | | 93.25 | | | | |
| NVP | | | | | 90 | 50 |
| VP | | | 92.7 | | | |
| MAA | | | | 70 | | 42 |
| TEDGMA | | | | 0.5 | | 0.75 |
| EDGMA | 1 | 1 | 1 | | 1 | |
| IPP | 0.2 | | | | | 0.2 |
| AIBN | | 0.25 | 0.3 | 0.3 | 0.25 | |
| PVA Fibers | 5.3 | | | | | 7.25 |
| PHEMA Fibers | | 5.25 | 5 | | 8.75 | |
| PVP Fibers | | | | 5 | | |

*IPP Isopropyl percarbonate
*AIBN azoisobutyronitrile

In each example above, electrospun fibers are made by dissolving 15% of the polymer in methanol and electrospinning the fibers as described previously. The weight of electrospun fiber is placed in a button mold, monomer composition from Table 1 added, vacuum pulled on the solution, button mold top added, and polymerized at 60° C. in an oven for 24 hours followed by curing at 80° C. for 4 hours. The button is removed and a lens machined from the button.

Drug Delivery System Utilizing Electrospun Fibers

The electrospun fibers may be loaded with a therapeutic drug and utilized as a drug delivery system. The fibers can be used as inserts in the eye, either separately or as a mat. The insert can be placed in the cul-de-sac of the eye in the form of dry fibers or a mat of dry fibers. This dry mat placed in the eye will hydrate thereby releasing the therapeutic drug as the mat hydrates. The fibers can also be inserted under the conjunctiva or sclera and will slowly erode away releasing the therapeutic drug, provided the fiber is not a crosslinked polymeric material.

These fiber mats may be stored dry, as noted above, which will minimize the loss of the therapeutic drug during storage. This will require that residual impurities such as monomers be kept to a minimum and that hydration time will be short. The fiber mats may also be stored in water or another solvent, which will remove impurities from the fiber mats. The storage solution must also contain a sufficient concentration of the therapeutic drug to prevent the drug from dissolving from the fibers while in storage.

This drug delivery system provides for the release of ophthalmic drugs from the fiber mat to an eye over an extended period of time, thus improving the efficacy of the drug by maintaining a therapeutic concentration of the drug in the eye for a long period of time. Known methods of delivering drugs to an eye typically result in initially high concentrations of drugs that quickly drop to levels which are too low for optimal efficacy. The electrospun fibers in the drug delivery system may be loaded with appropriate drugs via several methods described below. In some embodiments, the drugs may be selectively delivered to the front of the eye, the back of the eye, or both.

In a first method of loading the drug delivery system with appropriate drugs, the drugs are mixed with the polymer solution in the liquid well that feeds the electrospinning process. The concentration of the drug in the polymer solution will vary depending on the drug used and the rate and amount dispensed from the fibers when in use in the eye, and will need to be determined experimentally or otherwise for each drug and polymer combination. Typically ranges of drug concentration in the polymer solution may range from 0.1% to 30% by weight of the polymer solution. The drugs are dispensed with the polymer solution through the electrically-conducting liquid dispenser, and incorporated directly into the fibers created by the electrospinning process.

Polymer solutions for use in the drug delivery system include, but are not limited to, solutions having between 5 and 25 percent polymer by weight, similar to the base polymer solution utilized in the creation of the improved contact lens, with the addition of the therapeutic drug to be dispensed from the contact lens. The concentration of the drug in the contact lens and the rate of release in the eye are adjusted by altering the concentration of the drug in the polymer solution. More than one therapeutic drug may be added to the polymer solution to provide an improved contact lens that delivers a "cocktail" of drugs to the eye which may be tailored as necessary for the patient.

As an example of fiber mat formation, without limiting the range of parameters, mats for use with the drug delivery system described herein may be created by electrospinning PVA onto a flat rotating collector for 4 hours at a dispense rate of 1.8 ml per hour from an 18 gauge stainless steel needle situated 4 inches from the collector, and held at 30 kV DC from the collector. Varying the electrospinning time, the dispense rate, the needle gauge, the separation between dispenser and collector, and the dispenser potential are within the scope of the drug delivery system described herein, and the above described set of parameters is not limiting of the drug delivery system.

In a second method of loading the drug delivery matrix, the PVA mat is created, and then the mat is soaked in a solution containing the therapeutic drug. In this method, the therapeutic drug must be a water soluble drug. The amount of drug loaded into the fiber mat is dependent, among other parameters, on the soak time, the rate of uptake of the fibers, the fiber diameter, and the concentration of drug in the soak solution.

The rate of drug delivery from the fiber mats after placement in the eye is dependent, among other parameters, on the fiber diameter, the drug solubility in water, the amount of fiber in the mat (or lens), the amount of drug loaded in the fiber, and other parameters. The rate of drug delivery may also be controlled by changing the polymer composition from hydrophilic to hydrophobic, by treating the surface of the fibers to change the diffusion characteristics, by cross-linking the fibers and by coating the fibers with a polymer or other coating.

After the mats are created by electrospinning and subjected to drug-loading processing, if necessary, the mats may be coated with a polymer such as PVA by submersion in an aqueous solution of the polymer coating. They may also be crosslinked before and after the PVA coating.

An example of forming a fiber mat for drug delivery from electrospun fibers loaded with a therapeutic drug comprises the following steps. Dissolve 15% PVA in 5% moxifloxacin to methanol and electrospin into nanofibers. Place spun fibers in methanol containing 0.6% moxifloxacin for 2 hours and then dry the electrospun fibers. Form the spun fibers into a mat and store until use as an insert to place dry in the lower cul-de-sac of the eye.

A wide variety of therapeutic drugs may be spun into the fibers, so long as the drug is soluble in a solvent with the polymer solution. Examples of various types of drugs that may be spun into fibers include the following and any derivatives of the therapeutically-active agents which may include, but not be limited to: analogs, salts, esters, amines, amides, alcohols and acids derived from an agent of the invention and may be used in place of an agent itself.

Examples of the antibacterial antibiotics include, but are not limited to: aminoglycosides (e.g., amikacin, apramycin, arbekacin, bambermycins, butirosin, dibekacin, dihydrostreptomycin, fortimicin(s), gentamicin, isepamicin, kanamycin, micronomicin, neomycin, neomycin undecylenate, netilmicin, paromomycin, ribostamycin, sisomicin, spectinomycin, streptomycin, tobramycin, trospectomycin), amphenicols (e.g., azidamfenicol, chloramphenicol, florfenicol, thiamphenicol), ansamycins (e.g., rifamide, rifampin, rifamycin sv, rifapentine, rifaximin), β-lactams (e.g., carbacephems (e.g., loracarbef), carbapenems (e.g., biapenem, imipenem, meropenem, panipenem), cephalosporins (e.g., cefaclor, cefadroxil, cefamandole, cefatrizine, cefazedone, cefazolin, cefcapene pivoxil, cefclidin, cefdinir, cefditoren, cefepime, cefetamet, cefixime, cefmenoxime, cefodizime, cefonicid, cefoperazone, ceforanide, cefotaxime, cefotiam, cefozopran, cefpimizole, cefpiramide, cefpirome, cefpodoxime proxetil, cefprozil, cefroxadine, cefsulodin, ceftazidime, cefteram, ceftezole, ceftibuten, ceftizoxime, ceftriaxone, cefuroxime, cefuzonam, cephacetrile sodium, cephalexin, cephaloglycin, cephaloridine, cephalosporin, cephalothin, cephapirin sodium, cephradine, pivcefalexin), cephamycins (e.g., cefbuperazone, cefmetazole, cefminox, cefotetan, cefoxitin), monobactams (e.g., aztreonam, carumonam, tigemonam), oxacephems, flomoxef, moxalactam), penicillins (e.g., amdinocillin, amdinocillin pivoxil, amoxicillin, ampicillin, apalcillin, aspoxicillin, azidocillin, azlocillin, bacampicillin, benzylpenicillinic acid, benzylpenicillin sodium, carbenicillin, carindacillin, clometocillin, cloxacillin, cyclacillin, dicloxacillin, epicillin, fenbenicillin, floxacillin, hetacillin, lenampicillin, metampicillin, methicillin sodium, mezlocillin, nafcillin sodium, oxacillin, penamecillin, penethamate hydriodide, penicillin g benethamine, penicillin g benzathine, penicillin g benzhydrylamine, penicillin g calcium, penicillin g hydrabamine, penicillin g potassium, penicillin g procaine, penicillin n, penicillin o, penicillin v, penicillin v benzathine, penicillin v hydrabamine, penimepicycline, phenethicillin potassium, piperacillin, pivampicillin, propicillin, quinacillin, sulbenicillin, sultamicillin, talampicillin, temocillin, ticarcillin), other (e.g., ritipenem), lincosamides (e.g., clindamycin, lincomycin), macrolides (e.g., azithromycin, carbomycin, clarithromycin, dirithromycin, erythromycin, erythromycin acistrate, erythromycin estolate, erythromycin glucoheptonate, erythromycin lactobionate, erythromycin propionate, erythromycin stearate, josamycin, leucomycins, midecamycins, miokamycin, moxifloxacin, oleandomycin, primycin, rokitamycin, rosaramicin, roxithromycin, spiramycin, troleandomycin), polypeptides (e.g., amphomycin, bacitracin, capreomycin, colistin, enduracidin, enviomycin, fusafungine, gramicidin s, gramicidin(s), mikamycin, polymyxin, pristinamycin, ristocetin, teicoplanin, thiostrepton, tuberactinomycin, tyrocidine, tyrothricin, vancomycin, viomycin, virginiamycin, zinc bacitracin), tetracyclines (e.g., apicycline, chlortetracycline, clomocycline, demeclocycline, doxycycline, guamecycline, lymecycline, meclocycline, methacycline, minocycline, oxytetracycline, penimepicycline, pipacycline, rolitetracycline, sancycline, tetracycline), and others (e.g., cycloserine, mupirocin, tuberin).

Examples of the synthetic antibacterials include, but are not limited to: 2,4-diaminopyrimidines (e.g., brodimoprim, tetroxoprim, trimethoprim), nitrofurans (e.g., furaltadone, furazolium chloride, nifuradene, nifuratel, nifurfoline, nifurpirinol, nifurprazine, nifurtoinol, nitrofurantoin), quinolones and analogs (e.g., cinoxacin, ciprofloxacin, clinafloxacin, difloxacin, enoxacin, fleroxacin, flumequine, grepafloxacin, lomefloxacin, miloxacin, nadifloxacin, nalidixic acid, norfloxacin, ofloxacin, oxolinic acid, pazufloxacin, pefloxacin, pipemidic acid, piromidic acid, rosoxacin, rufloxacin, sparfloxacin, temafloxacin, tosufloxacin, trovafloxacin), sulfonamides (e.g., acetyl sulfamethoxypyrazine, benzylsulfamide, chloramine-b, chloramine-t, dichloramine t, $n^2$-formylsulfisomidine, $n^4$-β-d-glucosylsulfanilamide, mafenide, 4'-(methylsulfamoyl)sulfanilanilide, noprylsulfamide, phthalylsulfacetamide, phthalylsulfathiazole, salazosulfadimidine, succinylsulfathiazole, sulfabenzamide, sulfacetamide, sulfachlorpyridazine, sulfachrysoidine, sulfacytine, sulfadiazine, sulfadicramide, sulfadimethoxine, sulfadoxine, sulfaethidole, sulfaguanidine, sulfaguanol, sulfalene, sulfaloxic acid, sulfamerazine, sulfameter, sulfamethazine, sulfamethizole, sulfamethomidine, sulfamethoxazole, sulfamethoxypyridazine, sulfametrole, sulfamidocchrysoidine, sulfamoxole, sulfanilamide, 4-sulfanilamidosalicylic acid, $n^4$-sulfanilylsulfanilamide, sulfanilylurea, n-sulfanilyl-3,4-xylamide, sulfanitran, sulfaperine, sulfaphenazole, sulfaproxyline, sulfapyrazine, sulfapyridine, sulfasomizole, sulfasymazine, sulfathiazole, sulfathiourea, sulfatolamide, sulfisomidine, sulfisoxazole) sulfones (e.g., acedapsone, acediasulfone, acetosulfone sodium, dapsone, diathymosulfone, glucosulfone sodium, solasulfone, succisulfone, sulfanilic acid, p-sulfanilylbenzylamine, sulfoxone sodium, thiazolsulfone), and others (e.g., clofoctol, hexedine, methenamine, methenamine anhydromethylenecitrate, methenamine hippurate, methenamine mandelate, methenamine sulfosalicylate, nitroxoline, taurolidine, moxifloxacin, doxycycline, xibomol).

Examples of the antifungal antibiotics include, but are not limited to: polyenes (e.g., amphotericin b, candicidin, dennostatin, filipin, fungichromin, hachimycin, hamycin, lucensomycin, mepartricin, natamycin, nystatin, pecilocin, perimycin), others (e.g., azaserine, griseofulvin, oligomycins, neomycin undecylenate, pyrrolnitrin, siccanin, tubercidin, viridin).

Examples of the synthetic antifungals include, but are not limited to: allylamines (e.g., butenafine, naftifine, terbinafine), imidazoles (e.g., bifonazole, butoconazole, chlordantoin, chlormiidazole, clotrimazole, econazole, enilconazole, fenticonazole, flutrimazole, isoconazole, ketoconazole, lanoconazole, miconazole, omoconazole, oxiconazole nitrate, sertaconazole, sulconazole, tioconazole), thiocarbamates (e.g., tolciclate, tolindate, tolnaftate), triazoles (e.g., fluconazole, itraconazole, saperconazole, terconazole) others (e.g., acrisorcin, amorolfine, biphenamine, bromosalicylchloranilide, buclosamide, calcium propionate, chlorphenesin, ciclopirox, cloxyquin, coparaffinate, diamthazole di hydrochloride, exalamide, flucytosine, halethazole, hexetidine, loflucarban, nifuratel, potassium iodide, propionic acid, pyrithione, salicylanilide, sodium propionate, sulbentine, tenonitrozole, triacetin, ujothion, undecylenic acid, zinc propionate).

Examples of the antineoplastic agents include, but are not limited to: antineoplastc antibiotics and analogs (e.g., aclacinomycins, actinomycin fsub.1, anthramycin, azaserine, bleomycins, cactinomycin, carubicin, carzinophilin, chromomycins, dactinomycin, daunorubicin, 6-diazo-5-oxo-L-norleucine, doxorubicin, epirubicin, idarubicin, menogaril, mitomycins, mycophenolic acid, nogalamycin, olivomycines, peplomycin, pirarubicin, plicamycin, porfiromycin, puromycin, streptonigrin, streptozocin, tubercidin, zinostatin, zorubicin), antimetabolites exemplified by folic acid analogs (e.g., denopterin, edatrexate, methotrexate, piritrexim, pteropterin, Tomudex®, trimetrexate), purine analogs (e.g., cladribine, fludarabine, 6-mercaptopurine, thiamiprine, thioguanine), pyrimidine analogs (e.g., ancitabine, azacitidine, 6-azauridine, carmofur, cytarabine, doxifluridine, emitefur, enocitabine, floxuridine, fluorouracil, gemcitabine, tagafur).

Examples of the steroidal anti-inflammatory agents include, but are not limited to: 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, fluchloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone acetate, prednisolone 21-acetate, prednisolone 25-diethylamino-acetate, prednisolone sodium phosphate, prednisone, prednival, prednylidene, rimexolone, tixocortol, triamcinolone, triamcinolone acetonide, triamcinolone benetonide, and triamcinolone hexacetonide.

Examples of the non-steroidal anti-inflammatory agents include, but are not limited to: aminoarylcarboxylic acid derivatives (e.g., enfenamic acid, etofenamate, flufenamic acid, isonixin, meclofenamic acid, mefenamic acid, niflumic acid, talniflumate, terofenamate, tolfenamic acid), arylacetic acid derivatives (e.g., aceclofenac, acemetacin, aldlofenac, amfenac, amtolmetin guacil, bufexamac, cinmetacin, clopirac, diclofenac sodium, etodolac, felbinac, fenclozic acid, fentiazac, glucametacin, ibufenac, indomethacin, isofezolac, isoxepac, lonazolac, metiazinic acid, mofezolac, oxametacine, pirazolac, proglumetacin, sulindac, tiaramide, tolmetin, tropesin, zomepirac), arylbutyric acid derivatives (e.g., bumadizon, butibufen, fenbufen, xenbucin), arylcarboxylic acids (e.g., clidanac, ketorolac, tinoridine), arylpropionic acid derivatives (e.g., alminoprofen, benoxaprofen, bermoprofen, bucloxic acid, carprofen, fenoprofen, flunoxaprofen, flurbiprofen, ibuprofen, ibuproxam, indoprofen, ketoprofen, loxoprofen, naproxen, oxaprozin, piketoprolen, pirprofen, pranoprofen, protizinic acid, suprofen, tiaprofenic acid, ximoprofen, zaltoprofen), pyrazoles (e.g., difenamizole, epirizole), pyrazolones (e.g., apazone, benzpiperylon, feprazone, mofebutazone, morazone, oxyphenbutazone, phenylbutazone, pipebuzone, propyphenazone, ramifenazone, suxibuzone, thiazolinobutazone), salicylic acid derivatives (e.g., acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamide o-acetic acid, salicylsulfuric acid, salsalate, sulfasalazine), thiazinecarboxamides (e.g., ampiroxicam, droxicam, isoxicam, lomoxicam, piroxicam, tenoxicam), E-acetamidocaproic acid, s-adenosylmethionine, 3-amino-4-hydroxybutyric acid, amixetrine, bendazac, benzydamine, .alpha.-bisabolol, bucolome, difenpiramide, ditazol, emorfazone, fepradinol, guaiazulene, nabumetone, nimesulide, oxaceprol, paranyline, perisoxal, proquazone, superoxide dismutase, tenidap, bromfenac and zileuton.

Examples of anti-allergic agents include, but are not limited to: tranilast, ketotifen fumarate, pheniramine, diphenhydramine hydrochloride, sodium cromoglicate, bepotastine, epinastine HCl, olopatadine hydrochloride, levocombstine HCl, bromfenac and bepotastine besilate.

Examples of glaucoma-treating agents include, but are not limited to: pilocarpine hydrochloride, carbocal, latanoprost, travoprost, bimatoprost, betaxolol, levobunalol, timolol, iganipidine, brinzolamide, brimonidine and isopropylunoprostone.

Examples of antiviral agents include, but are not limited to: idoxuridine, acyclovir, ganciclovir and trifluorouridine.

Examples of anti-mycotic agents include, but are not limited to: pimaricin, fluconazole, miconazole, amphotericin B, flucytosine, and itraconazole.

Formation of the Improved Contact Lens

Once the fiber mats have been produced, they are incorporated into a contact lens as it is manufactured. Acceptable contact lens polymers for use in the improved contact lens, include, but are not limited to polyHEMA, polyHEMA/MA, polyHEMA/NVP/MMA, polyHEMA/MMA, polyHEMA/GMA, polyHEMA/PC, polyVA, polyHEMA/PVP/MA, polyHEMA/PVA/MA, poly MA/PVP, and polyHEMA/PVP/MMA, Poly GMA/MMA, polyHEMA/ACR, polyAA/HEMA, polyMMA/AA, polysilicone hydrogel, polyfluorocarbon hydrogel, and collagen. The lens polymer is preferably a homo or co-polymer of the monomer used to form the fiber mat.

In one method of fabricating the improved contact lens, the lens is formed individually by curing a monomer composition in a mold to polymerize the composition and create the contact lens. The electrospun fiber mat is cut into appropriately-sized sections or ground into appropriately-sized particles, and incorporated into the contact lens by inserting the mat section into the mold with the monomer composition prior to polymerization. The fibers are then polymerized with the monomer composition and are incorporated into the improved contact lens. In a second method of fabricating an improved contact lens, the fibers may be polymerized into a button or rod of polymer material by inserting the fibers into the appropriate mold and curing with monomers. The button or rod is then processed by cutting or polishing to produce the final improved contact lens.

The improved contact lens has superior physical characteristics as a result of the addition of the electrospun fibers into the lens. The improved contact lens may be fabricated with a thinner cross-section due to the increased mechanical strength and rigidity of the electrospun fiber materials. The thinner cross-section of the lens provides increased oxygen permeability while maintaining mechanical strength.

Fibers loaded with therapeutic drugs as described above may be used to manufacture the improved contact lens. When forming a contact lens using fibers that have been loaded with a therapeutic drug, the polymerization conditions and other processing steps must be controlled to prevent degradation of the therapeutic drug.

The electrospun fiber mats may be incorporated into a contact lens using other methods of contact lens fabrication. The previous examples of contact lens fabrication are illustrative of current contact lens fabrication techniques and methods of incorporating the fiber mat into those methods of fabrication. They are not intended to be limiting of the present invention.

The desired concentration of therapeutic drug in the target tissue determines the amount of drug to be loaded in the improved contact lens. The target tissue concentration can be increased by adding additional fibers to the contact lens or by increasing the concentration of the therapeutic drug in the solution from which the fibers are spun, or by the addition of therapeutic drug directly into the lens prepolymer solution.

Pharmaceutical Delivery and Surface Adsorption

The disclosed invention affords the ability to adsorb or absorb various chemical species to the electrospun fibrils to limit the adhesive ability of ocular proteins which can reduce optical acuity, affect wear comfort, and impede diffusive characteristics of the lens media. Further, the disclosed invention can be utilized to adsorb or absorb pharmaceutical agents that can be utilized for ocular treatment or medicative purposes. In this light, the electrospun lens is a specialized therapeutic lens that delivers chemical species over a prescribed period of time, to a localized portion of the cornea to effect ocular treatment.

Creating Electrospun Contact Lens Structures

The disclosed invention offers a means of fabricating contact lens structures that can be placed onto a recipient. In order to realize a suitable lens structure, fibrils of a suitable polymer, in one embodiment "Hema", must be created and layered to form the basis of a "mat" which exhibits the transparency and diffusion characteristics of corneal stromal tissue. In one embodiment, an electrospinning process produces the polymer fibrils. In this technique, the polymer under consideration, in this case collagen, is dissolved by a suitable solvent and injected under hydrostatic pressure into a conductive needle or capillary. A DC potential of preferably 4,000-12,000 volts is maintained between injection needle and a suitable target located at a distance away from the needle sufficient to preclude production of a coronal discharge or arc. The voltage is adjusted according to the distance and desired fiber diameter and structure. The voltage difference between the injection needle and target suited to the given solvent conductivity, polymer, and flow rate, and the resulting electrostatic field at the needle tip, results in the formation of a Taylor Cone from the tip of which issues a jet of a micron sized jet which is attracted to, and impacts with, the ground cathode target. It should be stated that the applied voltage on the needle could be either positive or negative depending on the situation. Additionally, the voltage does not have to be a constant polarity, as it has been previously shown by Dr. John B. Fenn ("Electrospray Dispersion in an Alternating Current Mode"—U.S. patent application Ser. No. 10/460,725, filed Jun. 11, 2003) that an alternating voltage prevents the charge buildup on electrospun fibers that contributes to a whipping instability. By simply alternating the applied needle voltage from a positive to a negative polarity, the electrospun fibers can be deposited at precise intervals to enable the construction of a precise electrospun "mat" of polymer material. This electrospun "mat" of polymer fibers could be constructed in such a way as to maintain mean fibril distance of approximately 200 nm ($10^{-9}$ meters). When evaporation of the solvent occurs from the electrospray jet, the result is fine micrometer ($10^{-6}$ meters) to nanometer ($10^{-9}$ meters) diameter polymer strands. The accumulation of such strands creates a "mat" of media having a diameter ranging from tens of microns or more down to tens of nanometers or less, depending on the concentration and nature of solute, the conductivity and viscosity of liquid, and the potential difference between the needle and target.

Collagen mats produced by this process can have diameters up to tens of millimeters and thickness of up to hundreds of microns, depending on deposition time. Similarly, it has been found that a variety of polymers for creating suitable lens structures can be derived from a variety of sources. It should be noted that extrusion rather than electrospinning of the polymer is an alternative in certain instances, along with laser ablation and chemical etching, to form the lens curvature. Laser cutting is often employed since fibril terminations must be severed and should not be excessively frayed or tangled. Tangling or fraying can affect bonding to native collagen and can vary optical transparency. While the resulting collagen "mat" consists of disorganized fibrils, this does not interfere with required transparency or diffusive characteristics. The general theory for corneal transparency has to do with the diameter of the collagen fibers in reference to the wavelength of the incident light. Organization of the fibers appears to be of less importance. This conclusion is supported by the fact that shark cornea exhibits regions of disorganized fibers and random interfibrillar distances while yet exhibiting a high degree of optical transparency. Use of microspun collagen fibers allows control of the fibril diameter, and the deposition rate determines the interfibrillar spacing. There are existing patents that explain how to make a solid homogenous membrane permeable by various means, one in particular is European Patent Number [EP 0 331 090 A2], Co-inventors Akira Ikushima, and Takeyuki Sawamoto, "Process for Producing Contact Lens", which describes how to create microfine holes in an already existing lens material. This is a random dispersal of holes, and does not come close to the degree of permeability of the disclosed invention, additionally, the prior method requires the use of an expensive, high powered particle accelerator with a subsequent chemical etching process. This method, although unique and innovative, is not commercially practical for producing a permeable contact lens. The disclosed invention has a superior method of obtaining permeability because it is made permeable from the ground up. From the very first collagen "mat" of fibrils, to the last, each "mat" is composed of a grid of collagen fibrils and not a solid surface of material. Traditional methods of making a contact lens permeable require that an existing solid lens be subjected to various processes that cause the creation of holes. The described invention has these "controllable" holes throughout each fibril "mat" of material. The hole infrastructure is built into the lens right from the start, not as a last step in the production line.

Electrospinning Controlled Polymer Fibril Matrices

Modification of the electrospinning process to yield a crosshatch pattern is achieved by maintaining either the needle anode at a fixed distance and moving the cathode target, or vice versa. Under normal conditions, the electrospun fiber is splayed about by the interplay of mechanical, hydrodynamic, and electrical forces so as to cause the polymer strand to accumulate on the target in a random pattern. While ordinarily this is not a problem in stromal scaffold "mat" construction, since the fiber diameter is the principal factor in transparency, there are instances where a regular matrix of stromal collagen is desired. By rapidly moving the needle in a linear direction for a fixed distance and then reversing such motion with respect to the target, while at the same time indexing the target utilizing a stepper motor drive or piezo stack or other such precision positioner, a series of relatively straight, parallel fibers may be laid down on the target surface. After the desired pattern has been achieved in one axis, the target may be rotated ninety degrees and the process repeated. The outer fringes of a mat matrix so created will be less organized than the central axis as the outer edge is where target position reversal occurs. This area can be trimmed away and discarded with a suitable laser. The resulting central scaffold area exhibits a structure, pattern, and diameter that closely mimics natural stromal collagen. If even greater accuracy is required in fibril spacing, the distance the fiber is deposited across a moving target can be increased and the jet shut down at the point of maximum travel. The target is then indexed to the next position, the electrospinning jet reestablished, and the target rapidly moved to the opposite extreme, where the process is repeated until the maximum linear coverage area of fibers in one axis of orientation is achieved. The target may then be rotated preferably ninety degrees as before and the spinning procedure repeated. The intent is to create a grid of horizontal and vertical fibers.

Improvements to the electrospinning process include utilizing a source of free ions to neutralize the charge on the surface of the polymer jet to minimize Coulomb repulsion and thus the extent of fiber splaying or whipping. In addition, alternating the jet high voltage polarity at high frequency can decrease fiber charging. When utilizing an electrospray setup for the purposes of electrospraying or electrospinning, one of the main expenses and a great percentage of the system is that of the hydrostatic feed system. Traditionally these are complicated, expensive, and sophisticated syringe pumps, capable of delivering a controlled and regulated amount of liquid, down to nanoliters [$10^{-9}$ L]. Dr. John B. Fenn proposed using a passive, self-regulating feed system in the form of a wick that operates via capillary action ("Method & Apparatus for Electrospray Ionization"—U.S. Pat. No. 6,297,499 B1, filed Jul. 3, 1998).

A continuous network of holes runs through the length of a glass wicking structure for a passive fluid delivery system. Although there exist several techniques for drilling or producing small holes in glass, there are limitations as to the size and depth of those holes. Most places that actually drill through the glass have a size limit of about 4 or 5 thousandths of an inch, and that is only good for about a ⅛ of an inch. A glass wick would require holes on the order of micrometers or sub-micrometers in diameter and running the entire length of the wick structure, with the length from as small as half an inch, to as long as several feet. If a laser is used to drill tiny holes in the glass structure, then the limitation of a short depth is encountered. To construct an acceptable wick with the desired capillary hole size ranging from several micrometers in diameter to as small as half a micrometer through the length of the glass structure, only one item has been found to fit the bill—Holey fibers. A U.S. Patent Application for using a Holey Fiber as a passive hydrostatic feed source for Electrospray Applications was previously filed (Inventor Michael E. Dziekan, Holey Optical Fiber for Electrospray Applications—U.S. Patent Application No. 60/511,237, filed Oct. 15, 2003). In addition to using a Holey Optical Fiber for Electrospray applications, another patent was previously filed that specifies their use as a method of drug delivery called "A Method of Synthesis and Delivery of Complex Pharmaceuticals, Chemical Substances and Polymers through the Process of Electrospraying, Electrospinning or Extrusion utilizing Holey Fibers by" Co-Inventors Michael E. Dziekan and Joseph J. Bango, U.S. patent application Ser. No. 11/000,723. Through the use of a co-axial arrangement of holes in a Holey Fiber, it is possible to produce a combination of chemicals that combine on-the-fly to form new types of polymers. The arrangement of Holey Fibers could be made in such a way as to permit even three or more component chemicals to be produced by a single combination fiber head. With this ability to send distinct chemicals through specific holes in the Holey Fiber, it would enable complex arrangements of polymers and drug combinations to be created. A coated polymer strand could be easily created, where it would be difficult by any other means. Besides the use of Holey Fibers, it is becoming more common to manufacture tiny electromechanical devices known as MEMs. These MEMs allow for intricate, self-contained, very small manufacturing plants to be constructed. A provisional patent has been filed, "A Method of Utilizing MEMS based devices to Produce Electrospun Fibers for Commercial, Industrial and Medical Use", Co-Inventors Joseph J. Bango and Michael E. Dziekan application Ser. No. 11/004,149.

First Aid Ophthalmic Lenses

Figure 3:
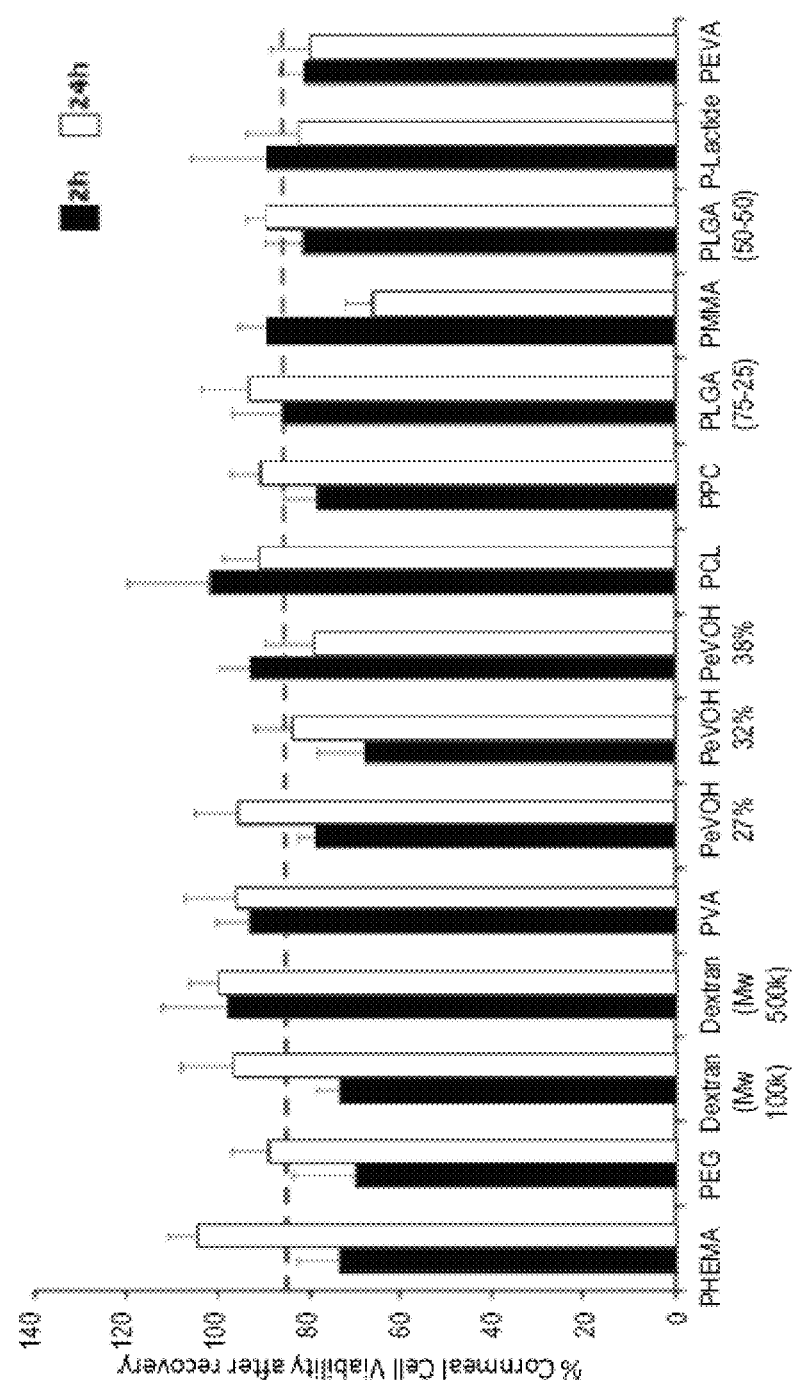
FIG. 3 shows average human cornea cell viability after a 24 h recovery following removal of raw polymer powders and replenishing with fresh media.

First-aid and healing lenses comprise two components: the lens materials, which are generally materials used in commercial lenses, and the electrospun nanofiber mat, which functions as the drug reservoir. To create a useful device out of these two materials, all the individual components have to be compatible with each other, requiring proper material selection (e.g. polymers and drug components), development of methods for a systematic assessment/testing of the fabricated devices, and instrumentation for carrying out the assessment/testing. Two electrospinners were built and used to prepare nanofibers from the selected polymer candidates. Each candidate was evaluated according to its stability, drug-loading capacity, and in vitro cytotoxicity against corneal cell lines (FIG. 3). Priority drugs were also identified with respect to their clinical relevance to a range of injuries where these lenses will be applied. Prednisolone 21-acetate, due to its superior stability and high corneal penetration was selected as a primary anti-inflammatory drug while Moxifloxacin, Doxycycline and Azithromycin were chosen as broad spectrum antibiotic drugs.

Alongside the preparation of drug-laden nanofibers, mechanical testing methods to evaluate tensile strength, oxygen permeability and geometries were also developed and validated. It was necessary to measure and verify that the physical properties of the contact lenses, both first-aid and healing, were conducive to the wound healing process and would provide good fit and function to the wounded cornea. Tests were conducted for mechanical properties, oxygen permeability, water content, refractive index and light transmission. These properties contribute to the comfort and ease of wear, as well as to the cornea health during extended wear of the lens.

Mechanical properties (specifically Young's modulus) should be assessed on a contact lens specimen using a tensile tester to conduct a pull test and should be completed in the appropriate physiological conditions (physiological saline at 37° C. per ISO Standard 18369). The test specimen should be a repeatable size and shape. Analysis of oxygen permeability, light transmission, and water content should be performed per ISO Standard 18369:2006 for repeatable and verifiable results. Oxygen permeability is assessed using the Fatt method for correcting boundary layer and edge effects. Water content of the contact lens is established by dehydrating the lens and measuring the moisture loss. This process is completed using an HR83 Mettler-Toledo Moisture Analyzer (Mettler-Toledo, Columbus, Ohio). Light transmission is measured using a spectrophotometer or other similar device and assessing the percentage of visible light that can pass through the lens material. The refractive index is measured using a CLR 12-70 Automatic Contact Lens Refractometer (Cambridgeshire, England).

Another important aspect in assessing performance of these devices was a valid and practical dissolution model for profiling release. In addition, analytical methods for analyses of drugs and drug combinations at low concentrations were developed. The initial methods of dissolution focused on using an orbital shaker in an incubator to circulate a known volume of solution containing the sample. The solution could then be extracted for analysis and then refilled at intervals allowing for drug release to be determined at various time points. This method of circulating the solution was chosen over a stationary solution in order to more accurately model the fluidics of the eye (which has a constant flow of solution over it). This method was successfully used for initial studies but, due to the large numbers of sample, solution changeovers needed to be conducted manually as there was inherent potential for error or variation from test to test. This led to the need for a more reproducible and controlled method of dissolution via automation of the dissolution process, which was accomplished with the use of commercially available dissolution systems produced by Agilent 400DS (Agilent Technologies, Santa Clara, Calif.). These dissolution systems provide better control of the exact time of sampling and a more precise temperature control. A method was developed for the Agilent dissolution system that would mimic the conditions on the eye. The temperature was maintained at body temperature (37° C.) but determining the flow rate past the sample was not as straight forward as selecting the temperature. The eye has a constant flow of liquid over it, which can vary if the eye is if damaged or not. This constant flow is not only intended to maintain hydration of the eye but also to act as a way of flushing the eye. This results in a constant removal of anything in the eye, including medications. Since the dissolution systems involve a stationary solution with the sample moving up and down within the solution, we cannot exactly mimic this flow of fresh solution past the samples. It was decided that a low dip rate would best mimic the slow gentle flow past the sample while replacing the solution at more frequent intervals initially (first 24 hours). Next, moving into daily extractions would best mimic the conditions these samples would experience in the eye. The more frequent initial replacement of the dissolution solutions was believed to be necessary to prevent concentration buildup during an initial burst release of medication from the samples. Since the eye is constantly refreshing itself with fresh tears, this buildup of concentration should be minimal in the actual eye, while a buildup of concentration in the dissolution solution during the burst could potentially slow the rate of release during passive diffusion, altering the kinetics from what would be experienced in the eye.

A method to analyze the samples for their drug content used a Waters H-Class Ultra-high Performance Liquid Chromatography instrument (UPLC, Waters Corporation, Milford, Mass.). The high pressure capability of this instrument (up to 15,000 psi) allowed for the use of columns with a very high number of theoretical plates, which results in a fast runtime for samples, typically 3-5 minutes. This shorter processing time allows for more samples to be analyzed in less time than would be possible with traditional HPLC, without sacrificing detection capabilities. A method for separating the medications from the other components in the samples was determined by finding the combination of solvents and flow rates that gave good separation of the components and minimal run times per sample. The UPLC was coupled with a Tunable Ultra-Violet (TUV) detector capable of detecting 2 wavelengths simultaneously, for quantification. This detector measured the absorbance at preset wavelengths which were determined to be the optimum wavelengths for examining the medications, and had high absorbance without interference.

The UPLC-TUV system was upgraded to include a sample organizer and a Tandem Quadrupole Mass Spectrometer (Waters XEVO TQD, Waters Corp., Milford, Mass.). The sample organizer allowed for 5 times as many samples to be loaded into the system at one time, while maintaining the samples under cooling in order to stabilize them while waiting to be run. This allowed for the system to be optimized for continual running, which resulted in more samples being analyzed in a given time period. The addition of the MS/MS gave a higher level of specificity for the desired analyte while also allowing for lower detection limits. Since the mass spectrometer quantifies based on a molecular mass and fragmentation pattern, it is less susceptible to interference from other compounds in the samples than the TUV (which relies on absorbance). This allowed for a more accurate quantization of the active pharmaceutical ingredients (APIs) (prednisolone-21-acetate, azithromycin, doxycycline, moxifloxacin) in the samples.

Figure 4:
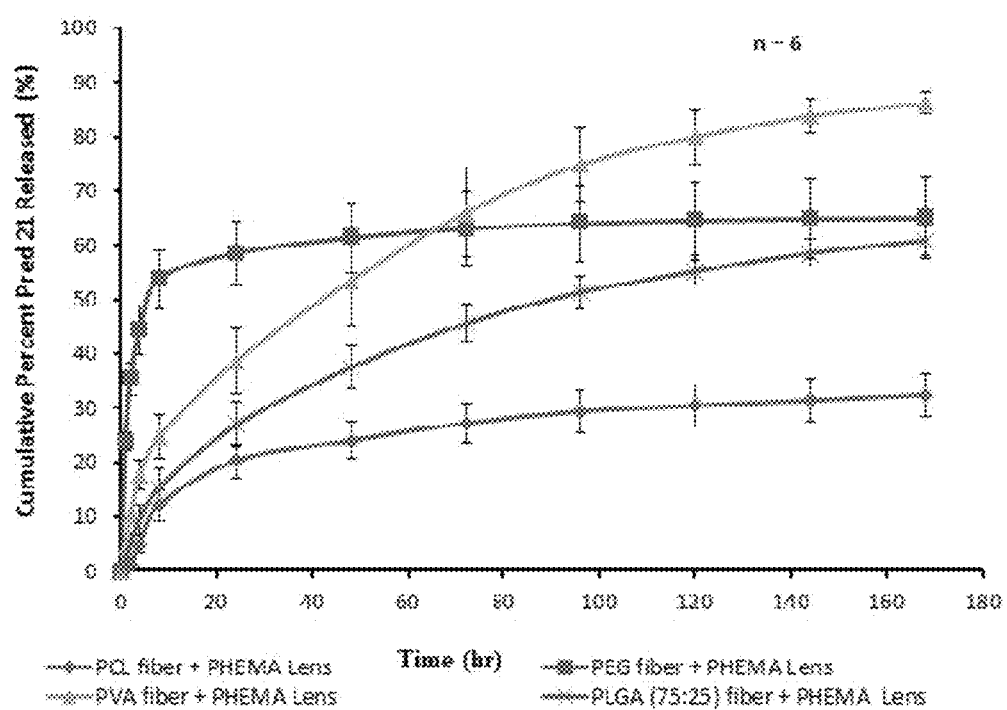
FIG. 4 shows prednisolone-21-acetate release kinetics from electrospun fiber made of polycaprolactone (PCL), poly-ethylene glycol (PEG), PVA, and PLGA 75:25 fabricated inside pHEMA contact lens.

Poly-2-hydroethyl methacrylate (polyHEMA) was chosen as the lens material to conduct drug-delivery testing, mainly due to its proven track record as a lens material, chemical compatibility with the polymers and drugs, and ease of lens fabrication suitable for laboratory testing. Several experiments were conducted to optimize lens fabrication methods using polyHEMA, which included varying initiator and cross-linker ratios, UV and thermal curing, and methods for incorporating nanofibers into the lens. Initial experiments were conducted using polyHEMA discs and eventually transitioned to the use of commercial contact lens molds (UCL Inc.). To increase drug payload, initial devices were made by embedding thin circular nanofiber mats of known mass into the lens mold during the lens curing process. FIG. 4 shows the drug release profiles of prednisolone 21-acetate loaded nanofibers embedded in actual contact lenses using polymers that were screened as viable candidates.

PolyHEMA-based lenses are limited to a water content of around 40%. Although this type of lens might be suitable for up to 3-day tests, it is not suitable for extended tests using a rabbit model. As a consequence, the lens platform was reformulated using methacrylic acid as an additive to improve water content and at the same time increase oxygen permeability across the lens. This resulted in a new formulation (L1030) that has higher water content and mechanical properties comparable to commercial lenses.

In vivo testing for multiple days with a rabbit model requires contact lenses that satisfactorily fit the rabbit eye. Otherwise, contact lenses would fall out, invalidating results. This difficulty was addressed by designing in-house molds adjusting for expansion factors of lens materials and incorporating geometric requirements of the rabbit in vivo tests. In preparation for in vivo testing with rabbits, a lens formulation was developed to accommodate test requirements. The main requirement for this test is comfort and fit for extended wear (7 days) of the lenses. In general, a desirable lens formulation would produce lenses with high water content and $O_2$ permeability. However, fit is determined based on the geometry of the molds used. After systematic variation of the different components of the lens prepolymer, such as initiator (AIBN), cross-linker (EGDMA), methacrylic acid (for increasing water content), and reaction temperature (below $T_g$ of nanofibers to prevent melting during polymerization), a suitable lens formulation (L1030) was prepared. All of the formulations were measured after being cured in a UCL (United Contact Lens, Arlington, Wash.) mold. The L1030 lens material produced at 60° C. is comparable to commercial lenses tested with respect to mechanical properties and oxygen permeability. In addition, no significant changes were observed to these values when nanofiber mats were incorporated into the contact lens. The modulus of the L1030 formulation is 0.49 MPa, which is very close to a 55% water content commercial polyHEMA lens (Ocufilcon C), which has a modulus of 0.46 MPa (measured). Ocufilcon C has an oxygen permeability of 18.77E-11 Dk (United Contact Lens), which is very comparable to that of L1030, at 16.7E-11 Dk. Overall (refer to Table 2), L1030 exhibits many of the same characteristics of a commercial contact lens with similar water content. The initial success of the L1030 formulation also allowed extended release testing. Azithromycin was deployed as the antibiotic drug for the development work.

In vitro cytotoxicity testing by the Center for Biomedical and Life Science (CBLS, Springfield, Mo.) of the L1030 control lenses was determined on primary human cornea cell cultures and NCI cells allowing for only 10% direct contact of lenses with cells. Lenses were in contact with cells for either 2 or 24 hours. In some conditions, cells were immediately assayed for cell viability while others were allowed to recover for 24 hours before assessing cell viability. All lenses incubated with human cornea cells exhibited similar reduced cell viability at the 2 and 24 hour time points. All cells were able to recover 24 hours after removal of the lenses from the media. No reduction of viability was observed on the NCI cells at any time point. In vitro cytotoxicity assays indicate the L1030 formulation is not cytotoxic after 2 and 24 hour incubation and 24 hour recovery tests. Using this lens formulation for preparing prednisolone 21-acetate loaded nanofiber mats indicated no significant change in cytokine expression when normalized with a standard contact lens. Two tests were conducted on commercial lenses to serve as a baseline comparison of results for the Ocular Irritation and Microbial Loading tests. Results indicated that there was no irritation observed for 1 or 3 days of continued wear with minimal irritation observed only after 7 days. In addition, the lenses tested did not affect the natural anti-bacterial properties of the eye.

The risk of environmental variables was reduced by preparing all lenses and lens materials under inert nitrogen atmosphere at relative humidities approaching zero. Each lens that was made was assessed for polymerized material, flexibility, stiffness, tackiness, ability to retain shape, brittleness and any other notable physical property that would set it apart from other batches. The formulation that was chosen from this process as the most probable for successful in vivo use was L1055 because it held its round shape consistently, is not hydrophobic and had less than 60% water content (for drug release).

The expansion of a disc of electrospun nanofiber mat when it is within the cured lens polymer may cause the lens to expand inconsistently. The geometry of a drug delivery nanofiber lens made from embedding a round disc of electrospun nanofiber mat into a molded lens varies from lens to lens and is rarely the typical spherical shape of a commercial contact lens. Electrospinning parameters were varied in an attempt to control mat expansion. Also, several methods of incorporating an embedded mat into the molded lens were employed, including pre-curing the mat in lens polymer, sandwiching the mat between two pre-cured lenses and incorporating manually cut mat into the lens. This last option yielded the best quality lenses, but the method of cutting the mats was not feasible for large production runs, leading to the development of a larger scale mat grinding process. Grinding methods were established to create fine particles while maintaining fibrillar structure in order to create a uniform distribution which will minimize the lens distortions, while still having the drug delivery benefit of the fibers in the lens. In one embodiment of the method, the whole mat is dipped in methanol and then frozen in liquid nitrogen. Once frozen, the mat is placed in the Micro-Mill grinder (Bel-Art, Wayne, N.J.) that maintains a liquid nitrogen flow while the mat is ground into particles. The particles are then dried in the vacuum oven overnight. To make lenses, the particles are sieved (#140 to #50, 100-300 µm, U.S. Standard Testing sieve) and then the particles are combined with the prepolymer solution. In other embodiments of the claimed processes and contact lenses, other methods of grinding may be used to prepare the particles.

In Vivo Ocular Irritation Testing on New Zealand White Rabbits.

Comfort and correct geometry of the lens for the test animals directly translates to the length of time the lenses stay on the eye. The incorporation of the drug delivery nanofiber mat presented physical irritation challenges that were addressed by in vitro cytotoxicity tests (CBLS), as well as surface and edge roughness studies. One drawback of molded lenses is the limitation imposed by the molds; only a single geometry specific to the mold can be made. This does not allow flexibility in rapid lens making for testing that requires specific geometries (e.g. fit for rabbits). To circumvent this issue, efforts were directed to use lathe-cut lenses where multiple lens geometries can be made from a single lens button. This approach required development of a new polyHEMA-based formulation suitable for making rods and evaluation of applicable curing parameters to achieve rods acceptable for adoption in the lathe-cutting process. Processing parameters as well as cure times and lathe-cutting specifications were developed and optimized.

A fabrication process for drug delivery lathe-cut lenses from polymer rods was optimized and tested. Drug delivery nanofiber mat loaded with azithromycin and prednisolone-21-acetate was electrospun and incorporated into the rods using an enhanced curing process that is specific to drug delivery materials. The lenses were lathe-cut from these rods and were tested for drug release and mechanical properties. A controlled study of varying AIBN concentrations and temperatures was completed in order to optimize hardness and bubble formation within the rods that are used for lathe-cutting into buttons for contact lens fabrication. Several concentrations of AIBN (initiator) were used with varying temperature parameters. In one embodiment, 0.05% AIBN initiator showed low bubble formation while still maintaining cure. After the curing method was established, various types of mat (PVA and PEVOH loaded with azithromycin and prednisolone-21-acetate) were added to the rod formulation with 0.05% AIBN (L1075) for further process optimization.

Once a rod-curing method was developed and it was established that the rods could be made with relatively few defects and were fully cured, six different types of rods were made to demonstrate the drug release capabilities of the lathe-cut lenses. These rods were separated into three production groups: prednisolone-21-acetate lens, azithromycin lens, and combination lenses.

The modulus of the drug delivery lenses is very comparable to the measured modulus of commercial HEMA lenses. The lenses should be strong but also flexible enough for a comfortable extended wear lens. The light transmissibility decreases slightly as the amount of mat in the lens increases; however, with a finer particle size, the light transmissibility of the lens increases. When comparing the light transmissibility of the lathe-cut lenses to the prednisolone-21-acetate molded lenses tested previously, it is vastly improved. This could be due to the enhanced surface finish of the lathe-cut lenses or possibly the uniformity of the mat in the lens. The water content of these lenses does not appear to be affected by the addition of mat. The lenses with three times the amount of mat have a very slight decrease in percent water.

TABLE 2

Mechanical testing data for drug-delivery lathe-cut lenses produced and tested.

| Lens ID | Description | % H2O | Light Transmissibility | O2 Permeability (Dk) | Modulus Average (Mpa) |
|---|---|---|---|---|---|
| LMD1079 | Pred: HEMA (0.05% AIBN) + Pred loaded PVA | 60.20% | 98.42% | 28.4E−11 +/− 4.6E−11 | 0.467 |
| LMD3002 | Pred/Pred: HEMA (0.05% AIBN with Pred) + Pred loaded PVA | 61.90% | 96.98% | 24.0E−11 +/− 2.0E−11 | 0.522 |
| LMD1080 | Azithro: HEMA (0.05% AIBN) + Azithro loaded PEVOH | 62.90% | 94.27% | 43.8E−11 +/− 8.4E−11 | 0.376 |
| LMD3003 | Azithro/Azithro: HEMA (0.05% AIBN with Azithro) + Azithro loaded PEVOH | 62.30% | 95.66% | 30.8E−11 +/− 9.1E−11 | 0.281 |
| LMD3004 | Pred/Azithro: HEMA (0.05% AIBN with Azithro) + Pred loaded PVA | 57.10% | 97.62% | 35.5E−11 +/− 9.9E−11 | 0.252 |
| LMD3005 | Azithro/Pred: HEMA (0.05% AIBN with Pred) + Azithro loaded PEVOH | 60.40% | 93.45% | 35.0E−11 +/− 11.6E−11 | 0.293 |
| LMD3002-0004 | 3xPred/Pred: HEMA (0.05% AIBN with Pred) + Pred loaded PVA(3x) | 58.40% | 97.01% | 63.3E−11 +/− 11.0E−11 | — |
| LMD3006 | 3xPred/Azithro: HEMA (0.05% AIBN with Azithro) + Pred loaded PEVOH(3x) | 60.40% | 88.43% | 51.9E−11 +/− 29.8E−11 | 0.593 |
| LMD3004-0003 | 3xPred/Azithro: HEMA (0.05% AIBN with Azithro) + Pred loaded PVA | 58.30% | 96.32% | 34.6E−11 +/− 3.4E−11 | — |
| LMD3008 | 3xAzithro&Pred/Pred: HEMA (0.05% AIBN with Pred) + Azithro loaded PEVOH(1x) + Pred loaded PVA(2x) | 56.60% | 91.98% | 56.7E−11 +/− 5.0E−11 | — |
| LMD1083 | 3xPred&Azithro/: HEMA (0.05% AIBN) + Pred & Azithro loaded PEVOH(3x) | 55.40% | 91.99% | 45.0E−11 +/− 14.9E−11 | — |
| Frequency 55 | Methafilcon A (19.7E−11 Dk) | — | — | 21.3E−11 +/− 3.0E−11 | 0.250 |

The amount of ground and sieved nanofiber particles was also optimized with respect to quality of the rods while maximizing drug release. Three times more nanofiber mat (in ground form than would have been incorporated in unground form) was incorporated into the rods to make lenses (LMD3002-0004, LMD3006 and LMD3004-0003) that exhibited satisfactory release without observable changes in rod quality. In addition, LMD3008 lenses showed that two different kinds of nanofiber mat (PVA and PEVOH) can be incorporated into the same lens and LMD1083 demonstrated that two different drugs can be incorporated into the same mat material (PEVOH). Table 3 illustrates the results of the mechanical testing showing the geometry and expansion factors.

The increase in mat (to three times the original amount) appears to have a positive effect on the oxygen permeability of the lenses. The higher oxygen permeability is uncharacteristic of a HEMA lens and will aid in the recovery of a corneal wound. Also, this is beneficial for an extended wear contact lens.

Table 3 shows the geometry and expansion factor that was measured for the lathe-cut lenses. The data shows that lenses with three times the amount of mat have a much tighter hydrated base curve. Because the de-blocking process involved water, the dry diameter could not be measured, but it is assumed that if the lathing parameters were not altered, then the expansion factor changes as the amount of mat increases.

Lenses were cut using the DAC DLL Series IV lathe (Firestone/Lens Dynamics, Kansas City, Mo.) with diamond tooling for roughing and finish. Standard speeds that are used on hydrogel buttons were used on the drug delivery buttons (0.2 inches thick with a 0.5 inch diameter). Buttons were blocked to collets using Misupco Hydroblock QR and were de-blocked using distilled water using a sonication bath for no more than thirty seconds. The dry lenses were cut to the following specifications and were then shipped with desiccant.

Figure 5:
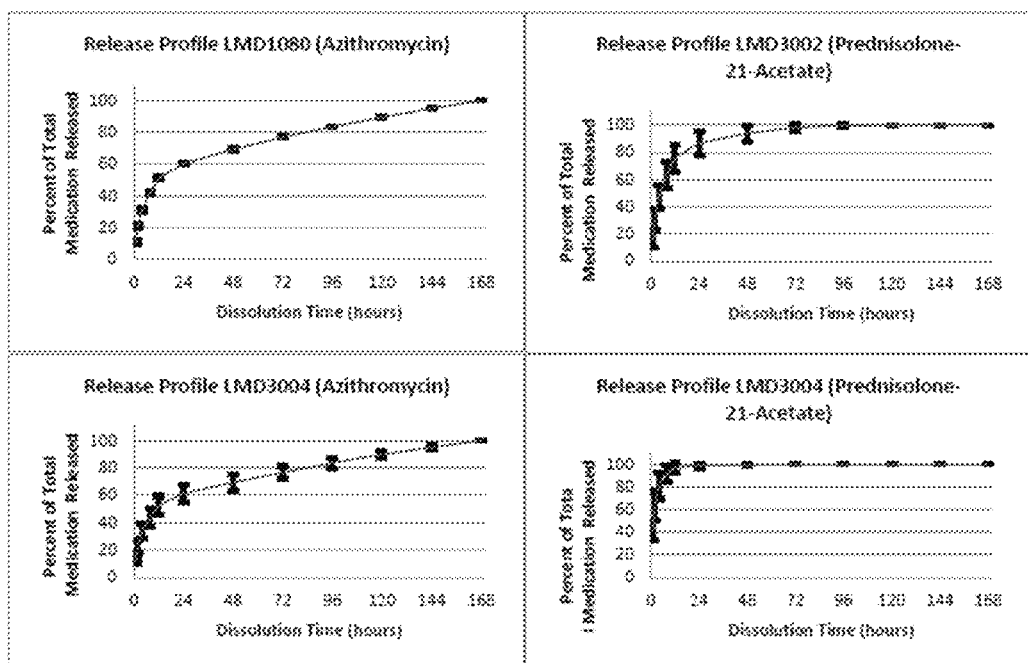
FIG. 5 shows drug-release profiles of lathe-cut lenses. Individual active component release, top row; combination therapy, bottom row. The release profiles shown were measure by UPLC-MS/MS and are based on an n=4.

0.2 mm center thickness
7.0 mm base curve
10.9 mm diameter
0.2 edge thickness
Single zone, Plano lens
1.3 expansion factor—thickness and radial The drug-release profiles of the lathe-cut lenses are presented in FIG. 5. LMD1080 delivers up to 7 days of Azithromycin (antibiotic) while LMD3002 exhibited up to 6 days of release of Prednisolone-21-acetate (anti-inflammatory). A combination lens (LMD3004) was also developed for delivering both the anti-inflammatory and the antibiotic drug from a single lens (FIG. 5 and Table 4). Based on the in vitro effective dose study conducted by CBLS (Western blots for MKP-1 on HeLa cells incubated with varying concentration of Prednisolone-21-acetate), in vitro effective dose can be extrapolated at about 5-10 ppm which is within the delivery range of these lathe-cut lenses. Azithromycin on the other hand has an $MIC_{50}$ and $MIC_{90}$ range of 1 to 256 ppm depending on a target bacterial pathogen (*Am. J. Opthalmol.* 145, 959-965, 2008). Current release profiles exhibited by these lathe-cut lenses fall in this range. It should also be noted that the test apparatus employs a 2.3 times greater rate of turnover than that of the average natural tear film.

TABLE 3

Hydrated geometry and expansion factor of drug-delivery lathe-cut lenses produced and tested.

| Lens ID | Description | Expansion Factor (diameter) | Hydrated Diameter (mm) | Hydrated Base Curve (mm) | Hydrated Thickness (mm) |
|---|---|---|---|---|---|
| LMD1079 | Pred: HEMA (0.05% AIBN) + Pred loaded PVA | 1.34 | 14.4 | 8.6 | 0.210 |
| LMD3002 | Pred/Pred: HEMA (0.05% AIBN with Pred) + Pred loaded PVA | 1.35 | 14.4 | 8.3 | 0.308 |
| LMD1080 | Azithro: HEMA (0.05% AIBN) + Azithro loaded PEVOH | 1.34 | 14.3 | 8.4 | 0.319 |
| LMD3003 | Azithro/Azithro: HEMA (0.05% AIBN with Azithro) + Azithro loaded PEVOH | 1.3 | 13.6 | 8.2 | 0.272 |
| LMD3004 | Pred/Azithro: HEMA (0.05% AIBN with Azithro) + Pred loaded PVA | H2O de-blocking | 13.9 | 8.4 | 0.313 |
| LMD3005 | Azithro/Pred: HEMA (0.05% AIBN with Pred) + Azithro loaded PEVOH | 1.32 | 14.2 | 8.4 | 0.333 |
| LMD3002-0004 | 3xPred/Pred: HEMA (0.05% AIBN with Pred) + Pred loaded PVA(3x) | H2O de-blocking | 14.0 | 7.8 | 0.334 |
| LMD3006 | 3xPred/Azithro: HEMA (0.05% AIBN with Azithro) + Pred loaded PEVOH(3x) | H2O de-blocking | 13.9 | 8.1 | 0.331 |
| LMD3004-0003 | 3xPred/Azithro: HEMA (0.05% AIBN with Azithro) + Pred loaded PVA | H2O de-blocking | 13.7 | 7.8 | 0.324 |
| LMD3008 | 3xAzithro&Pred/Pred: HEMA (0.05% AIBN with Pred) + Azithro loaded PEVOH(1x) + Pred loaded PVA(2x) | H2O de-blocking | 13.8 | 7.8 | 0.337 |
| LMD1083 | 3xPred&Azithro: HEMA (0.05% AIBN) + Pred & Azithro loaded PEVOH (3x) | H2O de-blocking | 13.8 | 8.6 | 0.318 |

TABLE 4

Summary of release profiles from lathe-cut lenses.
Detected Medication Release Time and Average Ranges

| | Prednisolone-21-Acetate | | Azithromycin | |
|---|---|---|---|---|
| LMD1080 | N/A | | 7 days | 3-1 ppm |
| LMD3002 | up to 6 days | 12 ppm-28 ppb | N/A | |
| LMD3004 | up to 3 days | 10 ppm-20 ppb | 7 days | 5-2 ppm |

These lathe-cut lenses also exhibited physical and mechanical properties comparable to commercial lenses of the same class. Furthermore, the results indicate that the oxygen permeability of these lenses is superior when compared to commercial lenses (Table 5).

TABLE 5

Physical properties of drug-delivering lathe-cut contact lenses.

| Lens Type | % Water Content | % Light Transmissibility | Refractive Index | Oxygen Permeability (Dk) | Modulus (MPa) |
|---|---|---|---|---|---|
| LMD1080 (Azithromycin Lens) | 62.90 | 94.27 | 1.402 | 43.8E−11 | 0.376 |
| LMD3002 (Prednisolone-21-Acetate Lens) | 58.40 | 97.01 | 1.399 | 24.0E−11 | — |
| LMD3004 (Combination, Prednisolone-21-Acetate + Azithromycin) | 58.30 | 96.32 | 1.401 | 34.6E−11 | — |

The drug-delivery lathe-cut lenses that were developed and optimized provided improved drug delivery performance for corneal wounds in the form of a first aid lens and a healing lens. The contact lens devices exhibited mechanical properties that are typical of a HEMA contact lens, with significant improvements in oxygen permeability.

First Aid and Wound-Healing Lenses

Drug-delivery contact lenses are specified to release active pharmaceuticals for an extended period. The first aid lenses will deliver an anti-inflammatory (e.g., Prednisolone-21-acetate), an antibiotic (e.g., Azithromycin), and a combination of both drugs in the specified time frame. On the other hand, wound healing lenses will deliver an anti-inflammatory and an antibiotic for a longer time period. The contact lenses developed have comparable mechanical properties to the same class rated for extended wear.

Contact Lens Specifications:
Physical Properties:
  Materials:
    Lens formulation: HEMA/MA with EGDMA cross-linker and AIBN initiator
  Nanofibers: LMD1080-PEVOH, LMD3002 and LMD3004-PVA
  Extended Wear—up to 3 days for first aid and up to 7 days for wound healing. Discard after use.
  Base Curves: B.4 mm (L1080) and 7.B mm (LMD3002 and LMD3004)
  Diameter: 14.3 mm (L1080), 14 mm (LMD3002) and 13.7 mm (LMD3004)
  Center Thickness: 0.319 mm (L1080), 0.334 mm (LMD3002) and 0.324 mm (LMD3004)
  Plano Lens, Single Zone

TABLE 6

Physical properties of drug-delivering lathe-cut contact lenses.

| Lens Type | % Water Content* | % Light Transmissibility | Refractive Index* | Oxygen Permeability (Dk) FATT Method* | Modulus (MPa) |
|---|---|---|---|---|---|
| LMD1080 (Azithromycin Lens) | 62.90 | 94.27 | 1.402 | 43.8E−11 | 0.376 |
| LMD3002 (Prednisolone-21-acetate Lens) | 58.40 | 97.01 | 1.399 | 24.0E−11 | — |
| LMD3004 (Combination, Prednisolone-21-acetate + Azithromycin) | 58.30 | 96.32 | 1.401 | 34.6E−11 | — |

*The physical properties of the drug delivery contact lenses are measured in accordance with ISO 18369:2006.

Drug Release: See Table 4.
Individual Release: See FIG. 5 top row.
Combination Therapy: See FIG. 5 bottom row.

Material Production and Processing:

Fabrication of the lenses incorporates a series of materials that are required to be made, processed and then combined. Initially, the process starts with the making of and incorporating medications into the electrospun nanofibers. These fibers are then processed before being used in the lens. The drug-loaded, processed mat and the lens formulation can then be combined to make the stock rod materials that will later be lathe cut into the lenses. In one embodiment of the process and contact lens claimed herein, an example process for creating the lens comprise the following steps.

Electrospun Mat Material:
Preparation of MD1047 mat
  Weigh out 0.26 g of Mowiol 18-88 into a glass vial.
  Weigh out 2.2 g of poly(vinyl alcohol) $M_w$ 130K, 99+% hydrolized (PVA) into a labeled centrifuge tube.
  Add 21 mL of 18M Ω Elga water to the glass vial containing the 0.26 g of Mowiol.
  Add stir bar to glass vial.
  Place in a hot water bath equilibrated at 90-100° C. and stir until dissolved.
  Add PVA to glass vial, and continue heating and stirring until dissolved.
    May need to vortex mix the solution several times to facilitate dissolution.
    May need to scrape PVA on the sidewalls of the vial back into solution.
  Once dissolved, sonicate for 15 minutes, cooling the solution to room temperature.
  Add 434 mg of Prednisolone-21-acetate to the vial, vortex, and sonicate again for 15 minutes.
  Electrospun at 30 KV, 0.80 mL/h, working d 17.5 cm and drum speed 300 rpm (3.2 mL×2 syringe per mat).

TABLE 7

Chemicals used for making MD1047

| Reagents | Vendor | Product # | CAS # | Quantity | % by mass (in mat) |
|---|---|---|---|---|---|
| Mowiol 18-88 | Sigma-Aldrich | 81365 | 9002-89-5 | 0.26 g | 9% |
| Poly(vinyl alcohol) 13K, 99% | Sigma-Aldrich | 563900 | 9002-89-5 | 2.2 g | 76% |
| 18M Ω Elga water | Mercy RnD | — | — | 21 mL | — |
| Prednisolone-21-Acetate | Sigma-Aldrich | P8650 | 52-21-1 | 434 mg | 15% |

Preparation of MD1052 mat:
  Weigh out 2.0 g of poly(vinyl alcohol-co-ethylene) (PEVOH) into a glass vial.
  Add 15 mL of 2-propanol to the glass vial containing the PEVOH.
  Add 6 mL of 18M Ω Elga water to the glass vial.
  Add stir bar to glass vial.
  Place in a hot water bath equilibrated at 90-100° C. and stir until dissolved.
    May need to vortex mix the solution several times to facilitate dissolution.
    May need to scrape PEVOH on the sidewalls of the vial back into solution.
  Once dissolved, sonicate for 15 minutes, cooling the solution to room temperature.
  Add 703 mg of Azithromycin dihydrate to the vial, vortex, and sonicate again for 15 minutes.
  Electrospin at 20 KV, 4.0 mL/h, working d=17.5 cm and drum speed=300 rpm (3.2 mL×2 syringe per mat).

TABLE 8

Chemicals used for making MD1052

| Reagents | Vendor | Product # | CAS # | Quantity | % by mass (in mat) |
|---|---|---|---|---|---|
| Poly(vinyl alcohol-co-ethylene) | Sigma-Aldrich | 414077 | 25067-34-9 | 2.0 g | 74% |
| 2-Propanol | Sigma-Aldrich | 2784575 | 67-63-0 | 15 mL | — |
| 18M Ω Elga water | Mercy RnD | — | — | 6 mL | — |
| Azithromycin | TCI | A2076 | 117772-70-0 | 703 mg | 26% |

Processing Electrospun Mat Material:
After electrospinning all mat types are then processed by grinding and sieving. Using a Scienceware Micro-Mill (Cat#372500000, Bel-Art, Wayne, N.J.),
  Connect the mill to a source of liquid nitrogen and allow the nitrogen to flow slowly.
  Once the mill has been cooled, the mat to be processed is dipped briefly in methanol and then dropped as a clump or ball directly into liquid nitrogen that has been poured into a suitable container.
  Place the frozen methanol/mat combination into the mill.
  Grind until the mat appears to be a powder without any noticeable larger clumps.
  Stop the flow of liquid nitrogen.
  Scrape the mat material (now in a powder like form) into a petri dish.
  Place in the vacuum oven overnight. In the oven, heat the mats to 40° C. for at least an hour and continuously pull vacuum (30 mm Hg) the entire time the mats are in the oven.

This process can be repeated for multiple mats by restoring the flow of nitrogen to the mill and repeating the process for additional mats and placing them in the oven. Ideally several mats are processed consecutively to reduce time and liquid nitrogen required to initially cool the mill. However, the number of mats that can be processed at one time can be limited due to icing on the mill, which is affected by the humidity in the room. The next day the mats can be removed from the oven and placed in the nitrogen flow desiccator until it is time to sift them.

Sifting the mats is performed by placing the sieves on the orbital shaker with aluminum foil under them to catch any material that may pass through the second sieve.
  Place the #50 sieve on top of the #140 sieve.
  Scrape the material to be processed from the petri dish onto the mesh of the #50 sieve. (Multiple mats can be added at one time.)
  Lay the plastic disk on top of the material and cover the sieves with aluminum foil to prevent loss.
  Turn the orbital shaker on at a high enough rate to cause the plastic disk to slide inside of the sieve. Periodically return to scrape unprocessed material that has collected on the side of the sieve and on top of the disk back onto the screen mesh.
  Collect the material that collects on the #140 sieve.

Allow the sieve to run until almost all of the material has been processed. The material that has been collected can be placed in vials and stored in a desiccator until it is ready to be used.

Lenses:

The lens prepolymer solution is prepared inside the nitrogen box. Table 9 gives the formulation for one embodiment referred to as L1075 based on a 45 ml batch. An example process of one embodiment of the invention is also described.

TABLE 9

Chemicals used for making in house lens formulation L1075

| Reagents | Vendor | Product # | CAS # | Quantity |
| --- | --- | --- | --- | --- |
| 2,2'-Azobisisobutyronitrile | Sigma-Aldrich | 441090-25G | 78-67-1 | 22.5 mg |
| 2-Hydroxyethyl methacrylate | Acros Organics | 156335000 | 868-77-9 | 43.2 mL |
| Ethylene glycol dimethacrylate | Sigma-Aldrich | 1001338930 | 97-90-5 | 450 µL |
| Methacrylic acid | Sigma-Aldrich | 1001370415 | 79-41-4 | 1350 µL |

Weigh the required mass of the AIBN into a 60 ml septa-seal amber vial using the analytical balance inside the nitrogen box.

Due to the sensitivity of the formulation to mass variation of the AIBN initiator, maintain a weighing tolerance of 0.3% error (e.g. if the target mass is 22.50, actual masses should be between 22.40-22.60 mg).

Pipette the required volumes of HEMA, MA, and EDGMA into the vial with the pre-weighed AIBN.

Mix the contents using the vortex mixer for 1 minute at 1750 rpm or until a solution is obtained.

Using the timer feature, sonicate for 5 minutes, using the degas setting on the instrument.

After sonication, if drug is required, add drug and stir bar, vortex and leave stirring until mat material is ready to be added.

The mat material is added to the pre-polymer solution by the IKA homogenizer. A "1×" loading is 750 mg of mat. A "3×" loading is 2250 mg of mat.

Once each batch is done homogenizing, it is placed in another 60 mL vial that is stirring to keep the material homogenous.

Next place vial on a stir plate while a vacuum is established (30 inches Hg) via the Schlenk line through a 19 gauge needle for 30 seconds.

Close the vacuum line and allow continuous stirring under vacuum (30 mm Hg) for two minutes.

The mixture is then transferred to a precut 9.5 inch long, MFA tube (⅝ inch ID McMaster-Carr 2133T7, Chicago, Ill.) and then sealed with a silicone stopper (⅝ inch ID McMaster-Carr 9283SK14) on one end. This step is done slowly to minimize induction of air pockets in the mixture.

A 0.5 inch void is left on the open end of the tube (if more than 0.5 inches is left, cut excess with a tubing cutter).

The open end is capped with another stopper using a syringe (without the plunger) to vent excess air while pushing the stopper. The stopper is secured as the last visible traces of bubbles are vented into the syringe.

The stoppers, in general, are pushed until they are approximately 0.5 inches into the tubing.

If multiple rods are the rods are continuously turned and inverted to maintain an even distribution of particles in the mixture.

In order to accommodate multiple-rod manufacturing simultaneously, a commercial hot dog roller (Top Dawg 6 Hot Dog Roller [Great Northern Popcorn Inc" MI], stripped of its internal components except the chain-drive and roller mechanism and connected to the high-temperature motor [Pitmann Express GM McMaster-Chicago, Ill.]) is used to turn the rods in order to keep the nanofiber mat particles homogenous in the rod. The roller is in the oven (Model 11-06060, Binder Inc" Bohemia, N.Y.) for the following a. 50 C—15 min
b. 55 C—15 min
c. 60 C—30 min
d. 65 C—75 min (1 hr, 15 min)
e. 80 C—15 min
f. 90 C—105 min (1 hr, 45 min)

Following cure, the rods are cooled in a nitrogen purged desiccator before being removed from the tube. The rods are cut into round buttons that are 0.5" in diameter and 0.2" long and then shipped to a contact lens lathing company and are lathed into contact lenses.

Lenses were cut using the DAC DLL Series IV lathe (CAI with diamond tooling for roughing and finish. Standard speeds that are used on hydrogel buttons were used on the drug delivery buttons (0.2 inches thick with a 0.5 inch diameter). Buttons were blocked to collets using Misupco Hydroblock QR (St. Paul Minn.) and were de-blocked using distilled water using a sonication bath for no more than thirty seconds. The dry lenses were cut to the following specifications and were then shipped to our lab dry with desiccant.

7.0 mm base curve
10.9 mm diameter
0.2 edge thickness
0.1 edge radius
Single zone, Plano lens
1.3 expansion factor—thickness and radial Testing and Methods for Evaluation of Prototype Physical Properties:

It is necessary to measure and verify that the physical properties of the contact lenses, both first-aid and wound-healing are conducive to the wound healing process and will provide good fit and function to the wounded cornea. Tests should be conducted for mechanical properties, oxygen permeability, water content, refractive index and light transmission. These properties contribute to the comfort and ease of wear of the lens. Analysis of mechanical properties (specifically Young's modulus), oxygen permeability, light transmission, refractive index and water content were performed as discussed above.

Three embodiments of drug-delivery lathe-cut lenses have been developed and assessed for drug delivery capabilities and mechanical properties. The three lens types are a Prednisolone-21-Acetate lens, an Azithromycin lens and a combination lens (containing both drugs). Dissolution testing determined that initially, Prednisolone-21-acetate did not have an extended release in the combination lenses (LMD3004 and LMD3005) or in the Prednisolone-21-Acetate lenses (LMD1079 and LMD3002). Three times more nanofiber mat was incorporated into the rods to make lenses (LMD3002-0004 [shown in Table 10], LMD3006 and LMD3004-0003 [shown in Table 10]) to achieve extended release. Also, LMD3008 lenses show that two different kinds of nanofiber mat (PVA and PEVOH) can be incorporated into the same lens and LMD1083 demonstrates that two different drugs can be incorporated into the same mat material.

The modulus and the refractive index of the drug delivery lenses is very comparable to that of commercial HEMA lenses. The lenses should be strong but also flexible enough for a comfortable extended wear lens. The light transmissibility decreases slightly as the amount of mat in the lens increases, but with a finer particle size, the light transmissibility of the lens increases. When comparing the light transmissibility of the lathe cut lenses to the Prednisolone-21-Acetate molded lenses tested previously, it is vastly improved. This could be due to the enhanced surface finish of the lathe cut lenses or possibly the uniformity of the mat in the lens. The water content of these lenses does not appear to be affected by the addition of mat. The lenses with three times the amount of mat have a very slight decrease in percent water but the correlation would need to be further explored with additional testing (larger sample sets).

The increase in mat (to three times the original amount) appears to have a positive effect on the oxygen permeability of the lenses. The higher oxygen permeability is uncharacteristic of a standard (having the same water content) polyHEMA lens and will aid in the recovery of a corneal wound. Also, this is beneficial for an extended wear contact lens.

The hydrated thickness, diameter and base curve of the lens should also be measured and adjusted to optimize fit, comfort and corneal health.

the quoted parameters and dimensional stability will also be influenced by the mechanical properties of the lens (2).

Young's modulus is the measure of how well a given material resists deformation, which makes it a great measure when comparing contact lens materials. Hydrogels, compared to other contact lens materials, have a very low Young's modulus, which offers some advantages. The way the lens drapes over the cornea means that the fit of the lens is not as dependent on the lens parameters, meaning enhanced fit on the eye. Given the flexibility of the lens, there is also a lower incidence of mechanically induced complications in the eye (2).

There are two basic lens designs: the single cut and the lenticular cut. The lenticular cut is used for most cast-molded lenses. The base curve of a soft lens is the central curvature on the posterior that fits against the cornea. Common base curve values range from 7.8 mm to 9.5 mm. The peripheral curve is located on the posterior surface of the lens towards the edge. This section is typically several millimeters flatter than the base curve of the lens and helps promote tear exchange under the lens. Typical peripheral curves range from 0.5 to 0.9 mm in width and 11 to 13 mm radially. Typical soft lens diameters range from 13 to 15 mm. Selection of lens diameter is important for cornea coverage (1). A typical adult rabbit cornea is unusually prominent and wide and measures approximately 15 mm in diameter, whereas a human cornea averages approximately 12 mm in diameter (horizontal) (3).

TABLE 10

This table shows the mechanical properties of drug-delivery lathe-cut lens samples.

| | Description | % H2O | Light Transmissibility | Refractive Index | $O_2$ Permeability (Dk) | Modulus (MPa) |
|---|---|---|---|---|---|---|
| Azithromycin | Azithro: HEMA (0.05% AIBN) + azithro loaded PEVOH | 62.90 ± 2.5 6% (n = 4) | 94.27 ± 1.166% (n = 4) | 1.402 ± 0.003 (n = 3) | 43.8E−11 ± 8.4E−11 (n = 4) | 0.376 ± 0.041 (n = 4) |
| Prednisolone-21-Acetate LMD3002 | 3xPred/Pred: HEMA (0.05% AIBN with pred) + pred loaded PVA(3x) | 58.40 ± 1.0 4% (n = 3) | 97.01 ± 0.907% (n = 2) | 1.399 ± 0.002 (n = 3) | 63.3E−11 ± 11.0E−11 (n = 4) | — |
| Combination: Prednisolone-21-Acetate & Azithromycin LMD3004 | 3xPred/ Azithro: HEMA (0.05% AIBN with azithro) + pred loaded PVA | 58.30 ± 1.0 9% (n = 3) | 96.32 ± 0.511% (n = 4) | 1.401 ± 0.005 (n = 3) | 34.6E−11 ± 3.4E−11 (n = 3) | — |

Lens Geometry

A good fit from a contact lens can most easily be achieved from a flexible hydrogel contact lens that drapes easily over the cornea and has minimal interaction with the eyelids during blinking. This fit, achieved by high levels of flexibility, is offset by the reduction in durability. Also, the rigidity of a material affects the flexure of a lens as well as the movement on the eye and tear exchange. The ease of manufacture of a contact lens, along with the reliability of Since soft contact lenses flex enough to allow one base curve to fit a range of corneal curvatures, many manufacturers provide soft lenses in only three base curves. The practitioner typically starts with the intermediate curve and then adjusts flatter or steeper based on the movement and appearance of the lens. Also, there are some lenses that are available in only one base curve and diameter which is used successfully in most patients. For an extended wear contact lens, it is typically recommended to have a loose fit. The loose fit allows for maximized tear exchange around the edges of the lens and permits removal of metabolic waste and epithelial debris that can accumulate during extended wear (1).

Table 11 below shows the geometry and expansion factor that was measured for the lathe cut lenses. The data shows that lenses with three times the amount of mat have a much tighter hydrated base curve. Because the de-blocking process involved water, the dry diameter could not be measured, but it is assumed that if the lathing parameters were not altered, then the expansion factor changes as the amount of mat increases.

Lenses were cut using the DAC DLL Series IV (DAC, Carpinteria, Calif.) lathe with diamond tooling for roughing and finish. Standard speeds that are used on hydrogel buttons were used on the drug delivery buttons (0.2 inches thick with a 0.5 inch diameter). Buttons were blocked to collets using Misupco Hydroblock OR (Misupco, St. Paul, Minn.) and were deblocked using distilled water using a sonication bath for no more than thirty seconds. The dry lenses were cut to the following specifications and were then shipped with desiccant.

0.2 mm center thickness
7.0 mm base curve
10.9 mm diameter
0.2 edge thickness
0.1 edge radius
Single zone, Plano lens
1.3 expansion factor—thickness and radial Drug Release Profiling:

Drug release profiling requires a combination of dissolution, to simulate the release from a biological system, and a method to quanitize the medication release.

Dissolution:

The eye has a constant flow of liquid over it which can vary if the eye is healthy or damaged. This constant flow is not only intended to maintain hydration of the eye but also to act as a way of flushing the eye, which results in a constant removal of anything in the eye, including medications. Since the dissolution systems involve a stationary solution with the sample moving up and down within the solution, we cannot exactly mimic this flow of fresh solution past the samples. It was decided that a low dip rate would best mimic the slow gentle flow past the sample while replacing the solution at more frequent intervals initially (first 24 hours) then moving into daily extractions would best mimic the conditions these samples would experience in the eye. The more frequent initial replacement of the dissolution solutions was believed to be necessary to prevent concentration buildup during an initial burst release of medication from the samples. Since the eye is constantly refreshing itself with fresh tears, this buildup of concentration should be minimal in the actual eye, while a buildup of concentration in the dissolution solution during the burst could potentially slow the rate of release during passive diffusion, altering the kinetics from what would be experienced in the eye. The dissolution of these samples was carried out using Agilent 400DS dissolution apparatus (Agilent Technologies, Santa Clara, Calif. under the following conditions:

Dissolution Cell temperature: 37° C.
Dip Rate—10 dips per minute (DPM)

TABLE 11

This table shows geometry and expansion factor of drug delivery lathe cut lens samples.

| | Description | Expansion Factor (diameter) | Hydrated Diameter (mm) | Hydrated Base Curve (mm) | Hydrated Thickness (mm) |
|---|---|---|---|---|---|
| Azithromycin LMD1080 (n = 8) | Azithro: HEMA (0.05% AIBN) + azithro loaded PEVOH | 1.34 | 14.3 ± 0.403 | 8.4 ± 0.183 | 0.319 ± 0.015 |
| Prednisolone-21-Acetate LMD3002 (n = 4) | 3xPred/Pred: HEMA (0.05% AIBN with pred) + pred loaded PVA(3x) | H2O de-blocking | 14.0 ± 0.126 | 7.8 ± 0.173 | 0.334 ± 0.020 |
| Combination: Prednisolone-21-Acetate & Azithromycin LMD3004 (n = 3) | 3xPred/ Azithro: HEMA (0.05% AIBN with azithro) + pred loaded PVA | H2O de-blocking | 13.7 ± 0.300 | 7.8 ± 0.493 | 0.324 ± 0.013 |

Overall, the lathe cut lenses with Azithromycin, Prednisolone-21-Acetate and a combination of both drugs have acceptable physical characteristics for a HEMA (55% water) contact lens, with improved oxygen permeability characteristics. The oxygen permeability of the contact lenses will couple with the drug release nanofibers to offer an improved option for administering drug to the cornea.

Dissolution Solution—10 mM Phosphate Buffer at a pH 7.4

Volume of Dissolution—3 ml

Sample extracted at time intervals from initial start time: 1 hr, 2 hr, 4 hr, 8 hr, 12 hr, 1 day, 2 days, 3 days, 4 days, 5 days, 6 days and 7 days Sample volume: 1 ml
Sample collections:
Room temperature in instrument
Removed daily and stored at 4° C. until analyzed
Stored in 2 ml amber HPLC Vials
Entire solution volume replaced after each sample extraction and replaced with fresh phosphate buffer.

These parameters are currently used to carry out the dissolution study of all lens samples. The purpose of this dissolution is to simulate the biological environment of drug release. Next the samples are transferred to other instrumentation for analysis. In the case of these materials the aliquots for each time point are transferred to UPLC-MS/MS for analysis.

The dissolution samples were analyzed and the drug content analyzed by a Waters H-Class UPLC coupled with a Waters Xevo TaD mass spectrometer (Waters Corporation, Milford, Mass.). The Waters H-Class is upgraded with a column manager and a sample organizer. The sample organizer is capable of maintaining a temperature of 4° C. The following UPLC parameters have been used for the analysis of each medication:

Prednisolone-21-Acetate:
Mobile Phase
Water—65%
Acetonitrile—30%
0.2% Formic Acid—5%
Flow rate—4 ml/min
Column—Waters Acuity CSH C18 Column, 130A, 1.7 J-lm, 2.1 mm×50 mm
Column Temperature—40° C.
Azithromycin
Mobile Phase
Water—75%
Acetonitrile—20%
0.2% Formic Acid—5%
Flow rate—4 ml/min
Column—Waters Acuity CSH C18 Column, 130A, 1.7 J-lm, 2.1 mm×50 mm
Column Temperature—40° C.

These parameters are utilized to aid in the separation of possible components while allowing the targeted medication to pass through the system to the detector as a single grouping but this is not the only method to ensure detection of the desired product. Additionally, the mass spectrometer has been tuned to optimize the detection of the desired medications. The mass spectrometer consists of two quadrapole; the first is capable of allowing only molecules of the mass corresponding to the medication that is being detected to pass through while other masses are deflected. The molecules that pass through the first quadrapole (corresponding to a single mass) are then fragmented and detected by the second quadrapole. This ensures detection of only the desired medication since molecules of different masses are deflected but molecules fragment uniquely depending on their structure. This allows for a high level of certainty that the quantitization is minimally affected by other compounds. These quantitized samples are then combined to derive the release profiles for the medications which allows for the evaluation of their performance.

The current prototypes are capable of releasing either Prednisolone-21-Acetate, Azithromycin or a combination of both for an extended period of time through passive diffusion (Table 4). The release rate of the medications are the result of many factors including drug loading, type of medication, lens formulation, lens thickness, mat loading and mat type. Table 4 shows current release time of each medication with respect to the lens type along with the concentration range that was detected.

Each factor is a variable that can affect how fast or how long the medications release from the lenses and can be used to fine-tune the release to the desired specifications. The release profiles of the current prototypes are shown in FIG. 5. These representations of the release profiles show the release in terms of a cumulative percentage of the total drug detected after the dissolution. In other words, 50% release at the 48 hour mark means that 50% of the total drug that the material released over 7 days has been released after 48 hours. The graphs also show the standard deviation of the sample set. It should be noted that not all samples of a specific sample type are shown in the graphs in FIG. 5.

References:
1. Contact Lenses: The CLAO Guide to Basic Science and Clinical Practice (Kendall/Hun, Dubuque, Iowa, 1995) vol. 1&2
2. K. French, Contact Lens Material Properties, Optician 230.6026 29-34 (2005)
3. A. Gwon, The Rabbit in Cataract/IOL Surgery in Animal Models in Eye Research, Tsonis, P. A., ed., (Elsevier, 2008) chap. 13. pp. 184-199.

Various therapeutic agents/drugs may be used in the contact lenses disclosed herein. In addition, drug combinations are contemplated for use in the drug-eluting contact lenses.

| Classification of drugs for use in the contact lenses |
|---|
| Antibiotics |
| Antihistamines |
| Anti-inflammatory agents |
| Anesthetic agents |
| Steroids |
| Non-steroidal anti-inflammatory drugs (NSAID) |
| Anti-viral agents |
| Anti-fungal agents |
| Anti protozoal agents |
| Autonomic agents |
| Anti-microbial agents |
| Anti-neoplastic agents |
| Antioxidants |
| Anti-glaucoma agents |
| Beta blockers |
| Carbonic anhydrase inhibitors |
| Prostaglandins |
| Anti-cholinergic |
| Anti-adrenergic |
| Anti-angiogenic agent (used for AMD treatment) |
| Anti-allergy agent |
| Mydriatics and cycloplegics agents |
| Dry eye treatment agent |

Ophthalmic Drug Combination Therapy

A combination of antibiotic+corticosteroid may be used as a class of drug combinations

| Brand Name | Manufacturer | Steroid | Antibiotic |
|---|---|---|---|
| Blephamide | Allergan | Prednisolone-21-acetate | Sodium sulfacetamide |
| Cortisporin | Monarch | Hydrocortisone | Neomycin, polymyxin B |
| FML-S | Allergan | Fluorometholone | Sodium sulfacetamide |

| Brand Name | Manufacturer | Steroid | Antibiotic |
|---|---|---|---|
| Maxitrol | Alcon | dexamethasone | Neomycin, polymyxin B |
| NeoDecadron | Merck | Dexamethasone | Neomycin |
| Poly-Pred | Allergan | Prednisolone-21-acetate | Neomycin, Polymyxin B |
| Pred-G | Allergan | Prednisolone-21-acetate | gentamicin |
| TobraDex | Alcon | Dexamethasone | Tobramycin |
| Vasocidin | Novartis | Prednisolone sodium phosphate | Sodium sulfacetamide |
| Zylet | Bausch + Lomb | Loteprednol | tobramycin |

Drug Combinations for the Treatment of Glaucoma:
    Classification of combinations:
    alpha agonists+beta blocker
    Prostaglandin+beta blocker
    Carbonic anhydrase inhibitors+beta blocker

| Brand name | Manufacturer | Drug I | Drug II |
|---|---|---|---|
| Combigan | Allergan | Brimonidine (Class: alpha agonists) | Timolol (Class: Beta Blocker) |
| Cosopt | Merck | Dorzolamide (Class: Carbonic anhydrase inhibitors) | Timolol (Class: Beta Blocker) |
| Azarga | Alcon | Brinzolamide (Class: Carbonic anhydrase inhibitors) | Timolol (Class: Beta Blocker) |
| DuoTrav | Alcon | Travaprost (Class: Prostaglandin) | Timolol (class: Beta blocker) |
| Xalacom | Pharmacia | Latanoprost (Class: Prostaglandin) | Timolol (class: Beta blocker) |
| Ganfort | Allergan | Bimatoprost (Class: Prostaglandin) | Timolol (class: Beta blocker) |

Drug Combination for Treatment of Allergy:
    Classification of combination: Ocular decongestants+antihistamine

| Brand name | Manufacturer | Drug I | Drug II |
|---|---|---|---|
| Naphcon-A | Alcon | Naphazoline (Class: ocular decongestants) | Pheniramine (Class: antihistamine) |

Drug Combination for Treatment of Non-Bacterial Blepharitis and Ocular Inflammation:

| Brand name | Manufacturer | Drug I | Drug II |
|---|---|---|---|
| DexaSite (ISV-305) | InSite Vision | Dexamethasone (class: corticosteroid) | Azithromycin (Class: Macrolide, antibiotic) |

Ophthalmic Drug Candidates:

Antibiotics:

Besifloxacin
Ciprofloxacin
Gentamicin
Neomycin
Bacitracin
Polymixin
Ofloxacin
Polytrim
Tobramycin
Erythromycin
Levofloxacin
Norfloxacin
Polymixin B
Sulfacetamide
Anti-glaucoma agents:
Beta Blockers:

Betaxolol
Levobunolol
Carteolol
Timolol
Metipranol
Carbonic anhydrase inhibitors:

Brinzolamide
Dorzolamide
Dichlorphenamide
Methazolamide
Acetazolamide
Prostaglandin:

Bimatoprost
Latanoprost
Tafluprsot
Unoprstone
Travapost
Cholinergics:

Pilocarpine
Other:

Apraclonidine
Brimonidine
Dipivefrin

| Anesthetics: | Corticosteroids: |
|---|---|
| Proparacaine | Dexamethasone |
| Tetracaine | Loteprednol |
| | Rimexolone |
| | Fluorometholone |
| | Prednisone |
| | Prednisolone-21-acetate |
| | Difluprednate |
| | rimexolone |

| NSAIDS: | Mydriatics and Cycloplegics: |
|---|---|
| Diclofenac | Atropine |
| Ketorolac | Homatropine |
| Flurbiprofen | Tropicamide |
| Bromfenac | Cyclopentolate |
| nepafenac | Phenylephrine |

| Anti-allergy | Anti-histamine |
|---|---|
| Alcaftadine | Pheniramine |
| Bepotastine besilate | |
| Emedastine | |
| Ketotifen Fumarate | |
| Lodoxamide tromethamine | |

| Anti-allergy | Anti-histamine |
|---|---|
| Olopatadine | |
| Azelastine | |
| Cromolyn sodium | |
| Epinastine | |
| Levocabastine | |
| Nedocromil | |
| Pemirolast | |

| Anti-angiogenics | Antivirals |
|---|---|
| Ranibizumab | Acyclovir |
| Bevacizumab | Valacyclovir |
| Verteprofin | Famciclovir |
| Aflibercept | Betadine |
| Pegaptanib | Ganciclovir |

| Anti-fungal | Anti protozoa agent |
|---|---|
| Natamycin | propamidine isetionate |
| Nystatin | Sulfadiazine |
| Amphotericin B | |
| Fluconazole | |
| Ketoconazole | |

| Dry eye treatment agent |
|---|
| Cyclosporine |
| Doxycycline |
| Loteprednol |
| Triglycerides |
| Lubricants based on Carboxymethylcellulose (Refresh), Hydroxypropyl cellulose (Lacriset), Sodium hylauronate (Vismed, Aquify), Polyethylene glycol and propylene glycol (Systane). |

STATEMENTS REGARDING INCORPORATION BY REFERENCE AND VARIATIONS

All references cited throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, and method steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. When a compound is described herein such that a particular isomer, enantiomer or diastereomer of the compound is not specified, for example, in a formula or in a chemical name, that description is intended to include each isomer and enantiomer of the compound described individually or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are described. Nothing herein is to be construed as an admission that the invention is not entitled to antedate such disclosure by virtue of prior invention.

Whenever a range is given in the specification, for example, a range of integers, a temperature range, a time range, a composition range, or concentration range, all intermediate ranges and subranges, as well as all individual values included in the ranges given are intended to be included in the disclosure. As used herein, ranges specifically include the values provided as endpoint values of the range. As used herein, ranges specifically include all the integer values of the range. For example, a range of 1 to 100 specifically includes the end point values of 1 and 100. It will be understood that any subranges or individual values in a range or subrange that are included in the description herein can be excluded from the claims herein.

As used herein, "comprising" is synonymous and can be used interchangeably with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" can be replaced with either of the other two terms. The invention illustratively described herein suitably can be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the invention has been specifically disclosed by preferred embodiments and optional features, modification and variation of the concepts herein disclosed can be resorted to by those skilled in the art, and that such modifications and variations are considered to be within the scope of this invention as defined by the appended claims.

We claim:

1. A process for forming a contact lens comprising the steps of electrospinning a mat of polymer fibers; applying a cross-linking treatment to the mat of polymer fibers; cooling the mat of polymer fibers; freezing the polymer fibers; processing the mat of frozen polymer fibers into particles, wherein the polymer fibers are kept frozen during processing into particles; isolating the particles having dimensions less than or equal to 500 micrometers, wherein isolating the particles includes sieving, gravity separation, electrostatic separation or combinations thereof; and incorporating the particles into a contact lens.

2. The process of claim 1 wherein the step of processing the mat of polymer fibers into particles further comprises the steps of milling, tearing, cutting, pulverizing or grinding the mat to produce particles comprised of polymer fibers; and drying the particles in a vacuum oven.

3. The process of claim 2 wherein the step of applying a cross-linking treatment to the mat of polymer fibers comprises placing the mat of polymer fibers in methanol.

4. The process of claim 3 wherein the step of freezing the polymer fibers comprises placing the mat of polymer fibers into a bath of liquid nitrogen.

5. The process of claim 2 wherein the step of drying the particles in a vacuum oven comprises heating the particles to 40° C. for at least one hour, and maintaining the particles in the oven for at least 6 hours.

6. The process of claim 2 wherein the step of incorporating the particles into a contact lens comprises the steps of combining the particles with a prepolymer solution, and preparing a contact lens from the prepolymer solution containing the particles.

7. The process of claim 6 wherein the step of preparing a contact lens comprises the steps of placing the prepolymer solution containing the particles in a mold, curing the prepolymer solution and particles to form a lens blank, and processing the lens blank to form a contact lens.

8. The process of claim 7 wherein the mold comprises a button or rod mold and the lens blank comprises a button or rod blank.

9. The process of claim 8 wherein the step of curing the prepolymer solution comprises continuously turning the mold while heating it to maintain an even distribution of the particles in the prepolymer solution during the curing step.

10. The process of claim 2 wherein the particles have dimensions between 100 micrometers and 500 micrometers.

11. The process of claim 2 wherein the particles have dimensions less than or equal to 100 micrometers.

12. The process of claim 2 wherein the concentration of the particles in the contact lens is between 0.01 percent by weight and 50 percent by weight.

13. The process of claim 2 wherein the concentration of the particles in the contact lens is at least 0.01 percent by weight.

14. The process of claim 2 further comprising the step of incorporating a therapeutic drug in or on the polymer fibers.

15. The process of claim 14 wherein the step of incorporating a therapeutic drug in or on the polymer fibers comprises soaking the polymer fibers in a solution containing the therapeutic drug.

16. The process of claim 14 wherein the step of incorporating a therapeutic drug in or on the polymer fibers comprises electrospinning the polymer fibers from a solution containing the therapeutic drug.

17. The process of claim 2 wherein particles from a plurality of mats of polymer fibers are incorporated into a single lens.

18. The process of claim 17 wherein each of the plurality of mats of polymer fibers incorporate a different therapeutic drug.

19. The process of claim 1 wherein the particles have a transmittance of at least 90% in the visible range of the electromagnetic spectrum.

20. The process of claim 14 wherein the therapeutic drug is eluted from the particles in situ for a period of at least 3 days.

21. The process of claim 14, wherein the therapeutic drug is selected from the group consisting of antibacterial antibiotic drugs, synthetic antibacterial drugs, antifungal antibiotic drugs, synthetic antifungal drugs, antineoplastic agents, steroidal anti-inflammatory agents, non-steroidal anti-inflammatory agents, antiallergic agents, glaucoma-treating agents, antiviral agents and anti-mycotic agents.

22. A contact lens prepared by the process of claim 1 where the polymer fibers have diameters between 1 nanometer and 2 micrometers.

23. The contact lens of claim 22 wherein the concentration of particles in the contact lens is at least 0.01 percent by weight.

24. The contact lens of claim 22 wherein the particles have a transmittance of at least 90% in the visible range of the electromagnetic spectrum.

25. The contact lens of claim 22 wherein the concentration of particles is sufficient to cause the lens to have an oxygen permeability of at least 15E-11 Dk.

26. The contact lens of claim 22 wherein the Young's modulus of the contact lens is between 0.10 MPa and 0.80 MPa.

27. A contact lens prepared by the process of claim 14 wherein the therapeutic drug is selected from the group consisting of antibacterial antibiotic drugs, synthetic antibacterial drugs, antifungal antibiotic drugs, synthetic antifungal drugs, antineoplastic agents, steroidal anti-inflammatory agents, non-steroidal anti-inflammatory agents, anti-allergic agents, glaucoma-treating agents, antiviral agents and anti-mycotic agents.

28. The contact lens of claim 27 wherein the therapeutic drug is eluted from the particles in situ for a period of at least 3 days.

29. The contact lens of claim 14 wherein the lens has an oxygen permeability of at least 30E-11 Dk.

30. The process of claim 1 further comprising the step of adjusting the concentration of particles incorporated into the contact lens to modify the oxygen permeability of the lens, wherein the oxygen permeability of the lens is at least 15E-11 to 75E-11 Dk.

31. The process of claim 9 further comprising the steps of cooling the mold and lens blank in a desiccator, removing the lens blank from the mold and cutting the contact lens from the lens blank.

32. The contact lens of claim 1 wherein the contact lens has a transmittance of at least 90% in the visible range of the electromagnetic spectrum.

33. The process of claim 14 further comprising the steps of modifying a parameter of the contact lens to achieve a desired period of in situ drug elution from the contact lens.

34. The process of claim 14 wherein the desired period of in situ drug elution is at least three days.

35. The process of claim 6 further comprising the step of incorporating a therapeutic drug in or on the polymer fibers of the mat.

36. The process of claim 35 further comprising the step of incorporating a therapeutic drug into the prepolymer solution prior to preparing a contact lens from the prepolymer solution.

37. A contact lens prepared by the process of claim 6 wherein a therapeutic drug incorporated in or on the mat of polymer fibers.

38. The contact lens of claim 37 wherein a therapeutic drug is added to the prepolymer solution prior to preparing a contact lens from the prepolymer solution.

39. The process of claim 9 wherein the step of curing the prepolymer solution comprises gradually increasing the temperature of the mold during the curing step.

40. The process of claim 17 wherein at least one of the plurality of mats of polymer fibers is formed from a different polymer than the other mats of polymer fibers.

* * * * *